(12) United States Patent
Nadig et al.

(10) Patent No.: US 11,260,027 B2
(45) Date of Patent: *Mar. 1, 2022

(54) DONOR ORGAN PRE-TREATMENT FORMULATION

(71) Applicant: MUSC FOUNDATION FOR RESEARCH DEVELOPMENT, Charleston, SC (US)

(72) Inventors: Satish Nadig, Johns Island, SC (US); Carl Atkinson, Mt. Pleasant, SC (US); Ann-Marie Broome, Mt. Pleasant, SC (US); Suraj K. Dixit, Charleston, SC (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 315 days.

This patent is subject to a terminal disclaimer.

(21) Appl. No.: 15/745,913

(22) PCT Filed: Jun. 24, 2016

(86) PCT No.: PCT/US2016/039315
§ 371 (c)(1),
(2) Date: Jan. 18, 2018

(87) PCT Pub. No.: WO2017/019214
PCT Pub. Date: Feb. 2, 2017

(65) Prior Publication Data
US 2018/0338963 A1 Nov. 29, 2018

Related U.S. Application Data

(60) Provisional application No. 62/198,197, filed on Jul. 29, 2015.

(51) Int. Cl.
| | |
|---|---|
| A61K 9/107 | (2006.01) |
| A61K 9/127 | (2006.01) |
| A61K 38/13 | (2006.01) |
| A61K 9/51 | (2006.01) |
| A01N 1/02 | (2006.01) |
| A61K 31/436 | (2006.01) |
| A61K 31/365 | (2006.01) |
| A61K 38/20 | (2006.01) |
| A61K 31/713 | (2006.01) |
| A61P 37/06 | (2006.01) |
| A61K 31/343 | (2006.01) |
| A61K 47/10 | (2017.01) |
| A61K 31/453 | (2006.01) |
| B82Y 5/00 | (2011.01) |

(52) U.S. Cl.
CPC .......... *A61K 9/1075* (2013.01); *A01N 1/0226* (2013.01); *A61K 9/127* (2013.01); *A61K 9/5146* (2013.01); *A61K 31/343* (2013.01); *A61K 31/365* (2013.01); *A61K 31/436* (2013.01); *A61K 31/713* (2013.01); *A61K 38/13* (2013.01); *A61K 38/2006* (2013.01); *A61K 38/2013* (2013.01); *A61K 47/10* (2013.01); *A61P 37/06* (2018.01); *A61K 31/453* (2013.01); *B82Y 5/00* (2013.01)

(58) Field of Classification Search
CPC ...... A61K 9/1075; A61K 9/51; A61K 9/1273; A61K 9/107; A61K 47/00; A61P 39/06
See application file for complete search history.

(56) References Cited

U.S. PATENT DOCUMENTS

| | | | |
|---|---|---|---|
| 4,789,633 A * | 12/1988 | Huang | A61K 9/127 264/4.1 |
| 5,817,333 A | 10/1998 | Kagayama et al. | |
| 6,013,256 A | 1/2000 | Light et al. | |
| 7,097,857 B2 | 8/2006 | Tracy et al. | |
| 7,304,033 B2 | 12/2007 | Larsen et al. | |
| 7,754,238 B2 | 7/2010 | Iversen et al. | |
| 8,236,329 B2 | 8/2012 | Kwon | |
| 8,613,951 B2 | 12/2013 | Zale et al. | |
| 2004/0225077 A1 | 11/2004 | Gravett et al. | |
| 2005/0013854 A1 | 1/2005 | Mannino et al. | |
| 2006/0210638 A1 | 9/2006 | Liversidge et al. | |
| 2008/0038353 A1 | 2/2008 | Lavasanifar et al. | |
| 2008/0138379 A1 | 6/2008 | Jennings-Spring | |
| 2008/0161423 A1 | 7/2008 | Kudo et al. | |
| 2008/0268061 A1 | 10/2008 | Jordan et al. | |
| 2010/0087474 A1 | 4/2010 | Kaushal et al. | |
| 2011/0059181 A1 | 3/2011 | Hu et al. | |
| 2012/0276133 A1 | 11/2012 | Maldonado | |

(Continued)

FOREIGN PATENT DOCUMENTS

| | | |
|---|---|---|
| WO | 1995015770 A1 | 6/1995 |
| WO | 0130377 A1 | 5/2001 |
| WO | 2005063213 A1 | 7/2005 |

(Continued)

OTHER PUBLICATIONS

Bowie et al. Science, 1990, 247:1306-1310 (Year: 2010).*

(Continued)

*Primary Examiner* — Vanessa L. Ford
*Assistant Examiner* — Sandra E Dillahunt

(57) ABSTRACT

Provided herein is a formulation to pre-treat an organ prior to transplantation, comprising a therapeutically effective amount of an immunosuppressive agent encapsulated in a micelle, liposome or polymeric nanoparticle that comprises on its surface a targeting moiety.

39 Claims, 14 Drawing Sheets

Specification includes a Sequence Listing.

(56) References Cited

U.S. PATENT DOCUMENTS

2013/0203041 A1 8/2013 Franklin et al.
2015/0079155 A1 3/2015 Jensen et al.

FOREIGN PATENT DOCUMENTS

| WO | 2012118376 A1 | 9/2012 | |
|----|---------------|--------|---|
| WO | 2015108912 A1 | 7/2015 | |
| WO | WO-2015108912 A1 * | 7/2015 | ........... C12N 15/117 |
| WO | WO-2016051536 A1 * | 4/2016 | ........... H04W 84/10 |
| WO | WO-2016057536 A1 * | 4/2016 | ........... A01N 1/0226 |

OTHER PUBLICATIONS

Burgess et al. J. Cell Biol. 111:2129-2138, 1990 (Year: 1990).*
Lazar et al. Mol. Cell. Biol., 8:1247-1252, 1988 (Year: 1988).*
Bork. Genome Research, 2000; 10:398-400 (Year: 2000).*
Nadig et al. RSC Adv, 2015; 5(54):43552-43562); Epub Apr. 24, 2015 (Year: 2015).*
Targeted Rapamycin Micelle (tram) As a Therapeutic and For Solid Organ Transplanthttp://musc.technologypublisher.com/technology/14993. Web published Apr. 4, 2014 (Year: 2014).*
Danhier et al. RGD-Based Strategies To Target Alpha(v) Beta(3) Integrin in Cancer Therapy and Diagnosis. Mol. Pharmaceutics, 2012; 9:2961-2973 (Year: 2012).*
Broome et al. Treating brain tumors with targeted-micelles containing rapamycin. [abstract]. In: Proceedings of the 105th Annual Meeting of the American Association for Cancer Research; Apr. 5-9, 2014; San Diego, CA. Philadelphia (PA): AACR; Cancer Res 2014;74(19 Suppl):Abstract nr 4467 (Year: 2014).*
Wang et al. Rapamycin-treated human endothelial cells preferentially activate allogeneic regulatory T cells. J Clin Invest. 2013; 123(4):1677-1693 (Year: 2013).*
Nadig et al. Towards Targeted Drug Delivery in Transplantation: Use of Nanoparticle Therapy. Transplantation: Jul. 15, 2014—vol. 98—Issue—p. 286-287 (Year: 2014).*
MUSC. Targeted Rapamycin Micelle (TRaM) as a Therapeutic and for Solid Organ transplant, Web published Apr. 4, 2014 (Year: 2014 ).*
Danhier et al. Mol. Pharmaceutics, 2012; 9:2961-2973 (Year: 2012).*
Nadig et al. Transplantation: Jul. 15, 2014—vol. 98—Issue—p. 286-287 (Year: 2014).*
The International Search Report and Written Opinion, dated Sep. 8,2016, in the corresponding PCT Application No. PCT/US2016/039315.
Liu et al. , "Pretreatment with intraluminal rapamycin nanoparticle perfusion inhibits neointimal hyperplasia in a rabbit vein graft model," Int J Nanomedicine. Oct. 21, 2010;5:853-60.
Wu et al., "A Combination of Donor Specific Transfusion and Rapamycin Prolonges Cardiac Allograft Survival in Mice," Transplant Proc. Dec. 2008;40(10):3699-701.
Dane et al., "Nano-sized drug-loaded micelles deliver payload to lymph node immune cells and prolong allograft survival," J Control Release. Dec. 10, 2011;156(2):154-60.
Kauffman et al., "Optimization of rapamycin-loaded acetalated dextran microparticles for immunosuppression," Int J Pharm. Jan. 17, 2012;422(1-2):356-63.
Bryant et al., "Nanoparticle delivery of donor antigens for transplant tolerance in allogeneic islet transplantation," Biomaterials. Oct. 2014;35(31):8887-94.
Khondee et al., "Targeted therapy of colorectal neoplasia with rapamycin in peptide-labeled pegylated octadecyl lithocholate micelles," J Control Release. Feb. 10, 2015;199:114-21.
Hasenstein et al., "Antitumor activity of Triolimus: a novel multidrug-loaded micelle containing Paclitaxel, Rapamycin, and 17-AAG," Mol Cancer Ther. Oct. 2012;11(10):2233-42.
Yáñez et al., et al., "Pharmacometrics and delivery of novel nanoformulated PEG-b-poly(epsilon-caprolactone) micelles of rapamycin," Cancer Chemother Pharmacol. Jan. 2008;61(1):133-44.
Ho-Chul Shin et al., "Pharmacokinetic study of 3-in-1 poly(ethylene glycol)-block-poly(D, L-lactic acid) micelles carrying paclitaxel, 17-allylamino-17-demethoxygeldanamycin, and rapamycin," J Control Release. Oct. 10, 2012;163(1):93-9.
Rouf et al., "Development and characterization of liposomal formulations for rapamycin delivery and investigation of their antiproliferative effect on MCF7 cells," J Liposome Res. 2009;19(4):322-31.
Federation Francophone de Cancerologie Digestive, Clinical Trial No. NCT01678664, "Everolimus After (Chemo) Embolization for Liver Metastases From Digestive Endocrine Tumors (EVACEL),", last updated Jan. 2, 2013.
Aadi et al., Clinical Trial No. NCT02009332, "Phase 1/2 Study of ABI-009 in Nonmuscle Invasive Bladder Cancer,", last updated Mar. 2, 2015.
Kirk, Parent Project No. 5R44HL102998-03, "Improved Adventitial Rapamycin Therapy for Peripheral Artery Restenosis," May 21, 2015.
Desai, Parent Project No. 3R42CA171552-01S1, "Investigation of a Nanoparticle Albumin-Bound Mtor Inhibitor, NAB-Rapamycin for T," May 21, 2015.
Forrest, Parent Project No. 5P20RR015563-10, "Nanoencapsulated Signal Transduction Inhibitors for Breast Cancer," May 22, 2015.
Latterich, Parent Project No. 1P01HL119165-01A1, "Antibody Targeted Therapeutics," May 21, 2015.

* cited by examiner

A

B

*P < 0.01

SEQUENCE LISTING

<160> NUMBER OF SEQ ID NOS: 7

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Gly Ser Gly Gly Gly Ser Gly Gly Gly Gly Ser
1               5                   10                  15

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Gly Ser
1               5

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Ser Gly Gly Gly Ser Gly Gly Gly Ser Gly Gly Gly Ser
1               5                   10                  15

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Ser
1

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Gly Gly Gly Gly
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic

```
        peptide

<400> SEQUENCE: 6

Ser Gly Gly Gly Gly Ser Gly Gly Gly Gly
1               5                   10

<210> SEQ ID NO 7
<211> LENGTH: 7
<212> TYPE: PRT
<213> ORGANISM: Homo sapiens

<400> SEQUENCE: 7

Val Ser Val Phe Pro Leu Glu
1               5
```

DONOR ORGAN PRE-TREATMENT FORMULATION

CROSS-REFERENCE TO RELATED APPLICATIONS

This application is a National Stage Application of PCT/US2016/039315 filed on Jun. 24, 2016, which claims priority from U.S. Provisional Patent Application No. 62/198,197 filed on Jul. 29, 2015. Each of prior mentioned applications is hereby expressly incorporated by reference herein in its entirety.

SEQUENCE LISTING

The instant application contains a Sequence Listing which has been submitted electronically in ASCII format and is hereby incorporated by reference in its entirety. Said ASCII copy, created on May 21, 2018, is named 112746-90791 (P1577)_SL.txt and is 1,823 bytes in size.

FIELD OF THE INVENTION

The invention is directed to a formulation, method and kit to pre-treat an organ prior to transplantation wherein the formulation comprises a therapeutically effective amount of an encapsulated immunosuppressive agent.

All publications, patents, patent applications, and other references cited in this application are incorporated herein by reference in their entirety for all purposes and to the same extent as if each individual publication, patent, patent application or other reference was specifically and individually indicated to be incorporated by reference in its entirety for all purposes. Citation of a reference herein shall not be construed as an admission that such is prior art to the present invention.

BACKGROUND OF THE INVENTION

Transplantation is a widely accepted and highly successful therapy for end-stage organ disease. While success rates and survival have risen steadily due largely to improved immunosuppression regimes, there is a growing appreciation that factors that occur early in the life of the graft significantly affect long-term survival. The donor organ is exposed to a series of injurious events prior to and during the transplant operative period, such as brain death, cold storage, cold and warm ischemia reperfusion. These events cause damage and immunologically prime the donor organ for allo-immune recognition. The removal, storage, and transplantation of a solid organ from a donor profoundly alter the homeostasis of the interior milieu of the organ. These effects impact how long the donor organ is delayed in returning to normal function after the transplantation is completed. The injury an organ sustains during recovery, preservation, and transplantation occurs primarily as a result of ischemia and hypothermia. Techniques for organ preservation serve to minimize this damage to promote optimal graft survival and function. Damage to donor organs prior to transplantation occurs in 2 main phases. The first (cold ischemic) phase, occurs when the organ is flushed in situ, then procured and preserved in a static or pulsatile hypothermic state prior to transplantation into the recipient. The second (warm ischemic) phase includes the time from organ removal from the preservation solution to the time it is sewn into the organ recipient.

As most transplanted organs are harvested from deceased donors, the organ must inevitably be stored until it can be transplanted into a suitable recipient. The donor and recipient are often in different locations (this can occur even when organs are harvested from living donors) and timing is critical while the donor organ is transported to the hospital where the recipient is being prepared for transplantation. Acceptable preservation times vary with the different organs. For example, most surgeons prefer to transplant heart and lungs within 5 hours of removal while kidneys can safely be stored for 24-48 hours, but earlier transplantation is preferred. Most pancreas transplants are performed after 5-15 hours of preservation. Liver transplants usually are performed within 6-12 hours. Over the last 20 years, a number of methods and solutions have been developed to preserve donor organs for transplantation. Collins et al. first introduced the simple cold storage technique to store and transport kidneys up to 30 hours. The development of the University of Wisconsin cold storage solution (UW-CSS) in 1986 improved organ preservation and resulted in a better understanding in preservation related injury. Various preservation solutions exist, each substantially different in their composition, but the purposes of each are similar: to prevent cellular edema, delay cell destruction, maintain organ metabolic potential, and maximize organ function after perfusion is reestablished.

Central to these immunological insults is the activation of donor endothelial and/or eptithelial cells (collectively "ECs") that, upon brain death, organ procurement, organ preservation, and reperfusion, promotes inflammation, cytokine and chemokine release and is central to the programming of recipient immune cells. It is appreciated that modulation of the endothelium and epithelium of the donor allograft prior to transplantation may improve graft outcomes. Recent studies have shown that treatment of ECs in vitro with the mTOR inhibitor rapamycin, an immunosuppressive drug used clinically, can render ECs tolerogenic. Pre-treatment of EC with rapamycin reduced proliferation of allo-reactive memory T cells, reduced cytokine production, reduced EC activation, and further promoted the differentiation of T regulatory cells in an EC/T cell co-culture system. These studies demonstrate that pre-operative rapamycin therapy provides protection from EC-mediated immune injury.

Conventional immunosuppression globally reduces the immunological response by dampening the entire immune system to protect the newly grafted organ. However, side effects such as infections, cancers, and metabolic derangements are among the list of complications that organ transplant recipients suffer while on the necessary organ saving immunosuppressant medications. Furthermore, these therapies have little impact on the cascade induced during IRI. While significant advancements have been made with the design and efficacy of newer immunosuppressive medications, such as rapamycin, many carry heightened systemic risk profiles. Therefore, a potential way to circumvent the systemic side effects of immunotherapeutics and protect the organ graft is to develop strategies to specifically deliver these medications directly to the endothelium of grafted tissues to reduce local injury, inflammation, allopresentation, and the harmful side effects associated with their systemic counterparts.

Currently available preservation solutions aim to stabilize organ metabolism, improve cell ion exchange, and improve cell membrane integrity, thereby facilitating prolonged organ storage, to allow for donor organ transportation. None of the currently available organ preservation solutions provide protection from inflammation or load immunosuppressive drugs into the donor organ prior to transplantation. For example, they do nothing to modulate the immunological injury suffered as a consequence of organ donation nor do they prepare the donor organ for the oncoming immunological attack by the recipient's immune system.

Therefore, a need exists in the art for novel additives to standard organ preservation solutions to prevent donor organ endothelial and epithelial activation, cytokine release, impair immune co-stimulation, and, thereby, reduce graft injury.

SUMMARY OF THE INVENTION

The present invention is directed to a formulation to pre-treat an organ prior to transplantation, comprising: a) a first composition comprising a therapeutically effective amount of an immunosuppressive agent encapsulated in a micelle, liposome or polymeric nanoparticle that comprises on its surface a targeting moiety; and b) a second composition comprising a preservation solution.

The invention is further directed to a method of pretreating an organ prior to transplantation with said formulation; and to a kit for producing the formulation.

DETAILED DESCRIPTION OF THE INVENTION

Figure 1:
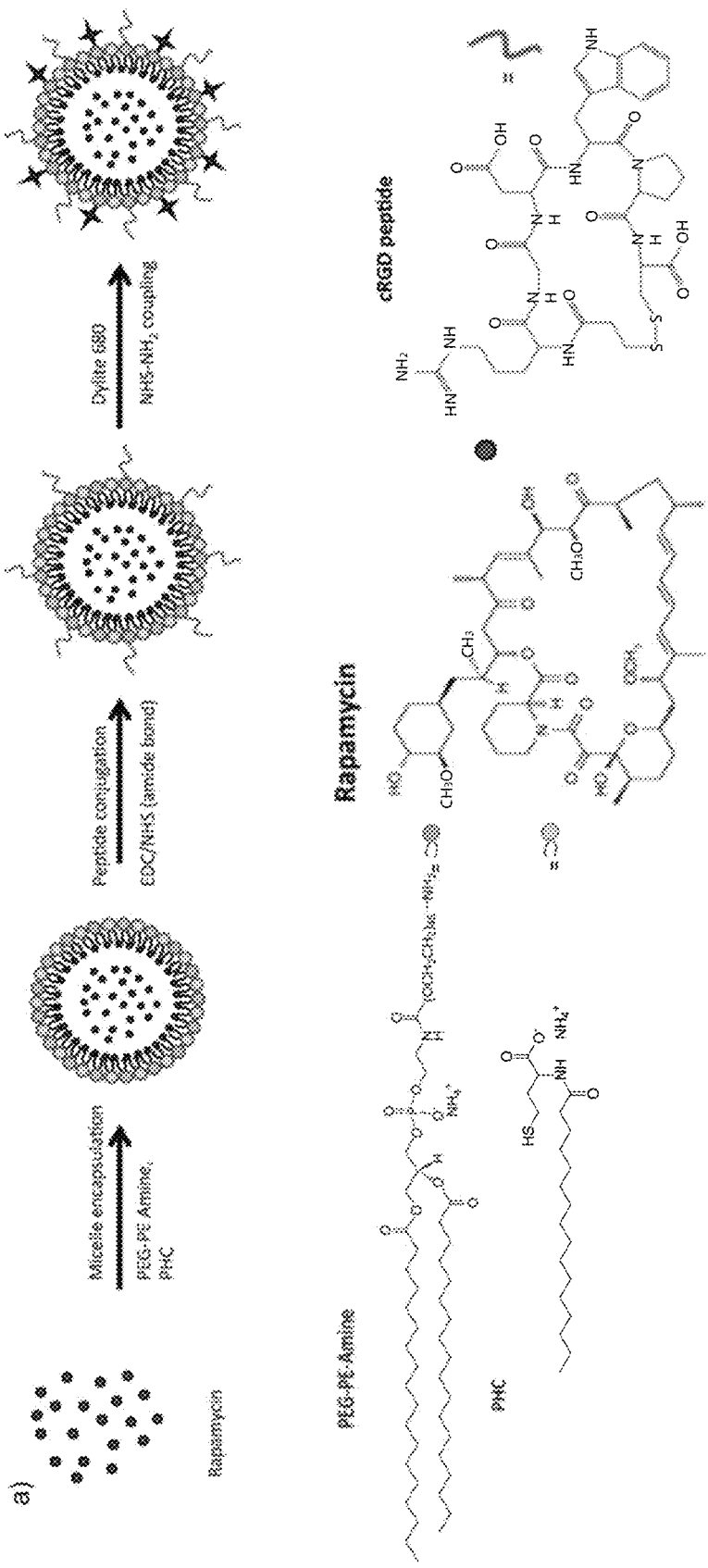
FIG. 1 shows the synthesis and characterization of rapamycin micelles. a) TRaMs are composed of rapamycin, NIR fluorophore (Dylight 680), and cRGD peptide targeting moiety for tracking and targeting purposes, respectively, b) Size calculation using DLS of RaM and TRaM demonstrates micelle sizes between 10-12 nm, c) UV-Vis spectroscopy of free rapamycin, RaM, and TRaM identifies rapamycin (275 nm) and Dylight 680 (692 nm). Concentration of each batch calculated based on the rapamycin peak. RaM and TRaM were assessed for stability over time in both phosphate buffered saline (d) and serum (e). Both NPs were able to maintain their composition over a 24 hours period.
Figure 1:
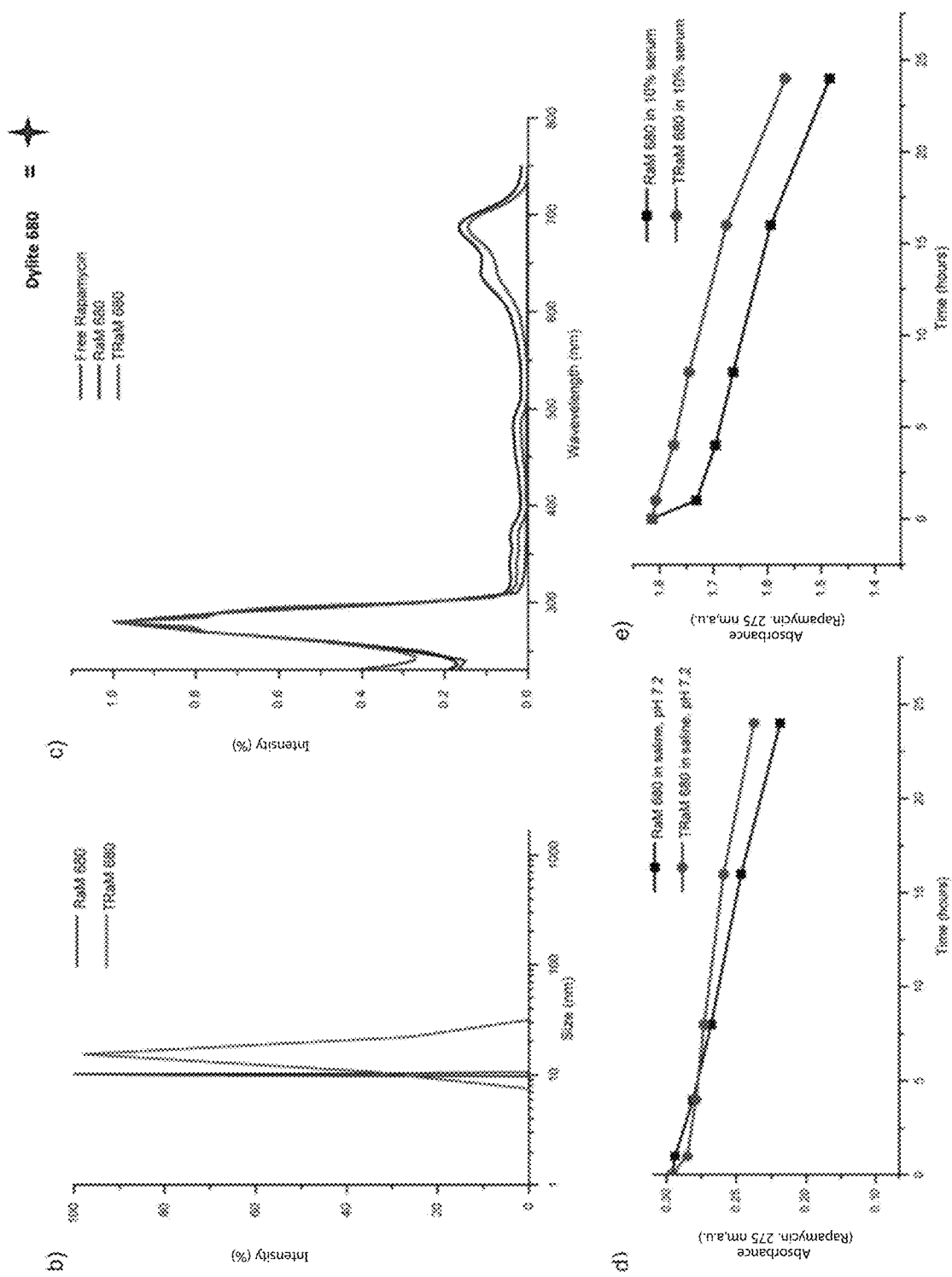

The invention provides for a bioengineering formulation to deliver, for example, an immunosuppressive agent such as rapamycin to the donor organ endothelial and/or epithelial cells (ECs). In one embodiment, addition of Targeted Rapamycin Micelles (TRaM) is added to standard organ preservation solutions such as, for example, University of Wisconsin solution. TRaM improves cellular penetration, as compared to untargeted rapamycin micelles (RaM), inhibits EC cytokine production, and significantly reduces MHC expression, as compared to free rapamycin drug or RaM, in in vitro models. In one embodiment, the micelles are decorated, for example, with cyclic Arginine-Glycine-Aspartate (cRGD) moieties to facilitate targeting to, for example, integrin alpha v beta 3 (αVβ3) on the EC and loaded with the immunosuppressive rapamycin.

Rapamycin, a potent mTOR inhibitor, was selected in one embodiment because of its ability to not only inhibit T cell effector cell functions, but also protect the endothelium. Studies have shown that rapamycin can modulate the upregulation of vascular endothelial growth factor, thereby conferring a protective effect on vascular endothelium, while also successfully attenuating endothelial injury and transplant vasculopathy in a humanized mouse aortic interposition graft model. (See C. Ponticelli, *Journal of nephrology,* 2004, 17, 762-768; and J. Hester, A. Schiopu, S. N. Nadig and K. J. Wood, *Am J Transplant,* 2012, 12, 2008-2016). Further, rapamycin may impede the emigration of passenger leukocytes to lymphoid organs, confirming that the release of rapamycin at the level of the organ itself may prevent the early IRI induced injury and further blunt alloimmune responses. (See H. Hackstein, T. Taner, A. F. Zahorchak, A. E. Morelli, A. J. Logar, A. Gessner and A. W. Thomson, *Blood,* 2003, 101, 4457-4463). In addition to rapamycin loading, micelles were also conjugated to near infrared (NIR) fluorophores for tracking studies.

Certain Definitions

The term "therapeutically effective" refers to the amount of the composition used is of sufficient quantity to ameliorate one or more causes or symptoms of a disease or disorder. Such amelioration only requires a reduction or alteration, not necessarily elimination. Data suggests a dose range of between 100-2000 ng/ml of TRaM in preservation solution will improve graft outcomes. In other embodiments of the invention, a dose range of 100 to 200 ng/ml, 200 to 300 ng/ml, 300 to 400 ng/ml, 400 to 500 ng/ml, 500 to 600 ng/ml, 600 to 700 ng/ml, 700 to 800 ng/ml, 800 to 900 ng/ml, 900 to 1000 ng/ml, 1000 to 1100 ng/ml, 1100 to 1200 ng/ml, 1200 to 1300 ng/ml, 1300 to 1400 ng/ml, 1400 to 1500 ng/ml, 1500 to 1600 ng/ml, 1600 to 1700 ng/ml, 1700 to 1800 ng/ml, 1800 to 1900 ng/ml and 1900 to 2000 ng/ml of Tram in preservation solution will improve graft outcomes.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient or an organ with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" or "suppress" refers to a treatment that forestalls or slows the onset of a disease or condition or reduced the severity of the disease or condition. Thus, if a treatment can treat a disease in a patient or an organ having symptoms of the disease, it can also prevent or suppress that disease in a patient or an organ which has yet to suffer some or all of the symptoms.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The terms "peptide," "protein," and "polypeptide" are used interchangeably to refer to a natural or synthetic molecule comprising two or more amino acids linked by the carboxyl group of one amino acid to the alpha amino group of another.

The term "protein domain" refers to a portion of a protein, portions of a protein, or an entire protein showing structural integrity; this determination may be based on amino acid composition of a portion of a protein, portions of a protein, or the entire protein.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA). The term "variant" refers to an amino acid or peptide sequence having conservative amino acid substitutions, non-conservative amino acid substitutions (e.g., a degenerate variant), substitutions within the wobble position of each codon (i.e. DNA and RNA) encoding an amino acid, amino acids added to the C-terminus of a peptide, or a peptide having 60%, 70%, 80%, 90%, or 95% homology to a reference sequence.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e g immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about 105 $M^{-1}$ with that second molecule.

The term "residue" as used herein refers to an amino acid that is incorporated into a polypeptide. The amino acid may be a naturally occurring amino acid and, unless otherwise limited, may encompass known analogs of natural amino acids that can function in a similar manner as naturally occurring amino, acids.

The term "position," with respect to an amino acid residue in a polypeptide, refers to a number corresponding to the numerical place that residue holds in the polypeptide. By convention, residues are counted from the amino terminus to the carboxyl terminus of the polypeptide.

A "fusion protein" refers to a polypeptide formed by the joining of two or more polypeptides through a peptide bond formed between the amino terminus of one polypeptide and the carboxyl terminus of another polypeptide. The fusion protein may be formed by the chemical coupling of the constituent polypeptides or it may be expressed as a single polypeptide from nucleic acid sequence encoding the single contiguous fusion protein. A single chain fusion protein is a fusion protein having a single contiguous polypeptide backbone.

The term "specifically deliver" as used herein refers to the preferential association of a molecule with a cell or tissue bearing a particular target molecule or marker and not to cells or tissues lacking that target molecule. It is, of course, recognized that a certain degree of nonspecific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include P-alanine, L-a-amino butyric acid, L-7-amino butyric acid, L-a-amino isobutyric acid, L-e-amino caproic acid, 7-amino heptanoic acid, L-aspartic acid, L-glutamic acid, N-E-Boc-N-a-CBZ-L-lysine, N-E-Boc-N-a-Fmoc-L-lysine, L-methionine sulfone, L-norleucine, L-norvaline, N-a-Boc-N-KBZ-L-ornithine, N-6-Boc-N-a-CBZ-L-omithine, Bocp-nitro-L-phenylalanine, Boc-hydroxyproline, and Boc-L-thioproline.

The term "percent (%) sequence identity" or "homology" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

Certain Embodiments of the Invention

In one embodiment of the invention, provided is a formulation to pre-treat an organ prior to transplantation, comprising:
a) a first composition comprising a therapeutically effective amount of an immunosuppressive agent encapsulated in a micelle, liposome or polymeric nanoparticle that comprises on its surface a targeting moiety; and
b) a second composition comprising a preservation solution.

In another embodiment of the present invention, provided is a formulation wherein said immunosuppressive agent comprises a mammalian target of rapamycin inhibitor, a calcineurin inhibitor or a combination thereof.

In another embodiment of the present invention, provided is a formulation wherein said immunosuppressive agent is rapamycin or a derivative thereof or combinations thereof.

In another embodiment of the present invention, provided is a formulation wherein the immunosuppressive agent comprises tacrolimus or a derivative thereof or combinations thereof.

In another embodiment of the present invention, provided is a formulation wherein the immunosuppressive agent comprises cyclosporin A or a derivative thereof or combinations thereof In another embodiment of the present invention, provided is a formulation wherein the immunosuppressive agent comprises a nuclear factor kappa-light-chain-enhancer of activated B cells (NFkB) inhibitor.

In another embodiment of the present invention, provided is a formulation wherein the immunosuppressive agent comprises a Janus kinase 3 (JAK3) inhibitor.

In another embodiment of the present invention, provided is a formulation wherein the immunosuppressive agent comprises Interleukin 2 (IL-2) R alpha or a derivative thereof or a combination thereof.

In another embodiment of the present invention, provided is a formulation wherein the immunosuppressive agent comprises Complement C siRNA.

In another embodiment of the present invention, provided is a formulation wherein said immunosuppressive agent is encapsulated in a micelle.

In another embodiment of the present invention, provided is a formulation wherein the immunosuppressive agent comprises mycophenolate or a derivative thereof or a combination thereof.

In another embodiment of the present invention, provided is a formulation wherein said nanoparticle encapsulating said immunosuppressive agent has a mean diameter of 5 nm to 100 nm.

In another embodiment of the present invention, provided is a formulation wherein said nanoparticle encapsulating said immunosuppressive agent has a mean diameter of 10 nm to 15 nm.

In another embodiment of the present invention, provided is a formulation wherein said nanoparticle is pH sensitive, temperature sensitive or combinations thereof.

In another embodiment of the present invention, provided is a formulation wherein the micelle comprises N-palmitoyl homocysteine.

In another embodiment of the present invention, provided is a formulation wherein the micelle comprises amino-polyethylene glycol-phosphatidylethanolamine.

In another embodiment of the present invention, provided is a formulation wherein said targeting moiety is a peptide or peptidomimetic that binds Complement component 3 (C3) breakdown products and reperfusion epitopes, a peptide or peptidomimetic that binds an integrin, or combinations thereof.

In another embodiment of the present invention, provided is a formulation wherein said targeting moiety comprises the amino acid sequence Arg-Gly-Asp.

In another embodiment of the present invention, provided is a formulation wherein said targeting moiety comprises a cyclized Arg-Gly-Asp peptide or peptidomimetic.

In another embodiment of the present invention, provided is a formulation wherein said preservation solution is selected from the group consisting of Belzer UW Cold Storage Solution, Viaspan, CoStorSol, Kyoto ET Solution, Celsior Solution, Phosphate Buffered Sucrose Solution, Bretschneider Histidine Tryptophan Ketoglutarate (HTK) Solution, Ross-Marshall Citrate Solution, Euro-Collins Solutions and Perferdex.

In another embodiment of the present invention, provided is a formulation wherein TRaM or Free Rapamycin will be added at a dose from 100 ng/ml to 2000 ng/ml.

In another embodiment of the invention, provided is a method for pre-treating an organ prior to transplantation, comprising the step of administering to said organ in need thereof a therapeutically effective amount of a formulation comprising a first composition comprising a therapeutically effective amount of an immunosuppressive agent encapsulated in a micelle, liposome or polymeric nanoparticle that comprises on its surface a targeting moiety; and a second composition comprising a preservation solution.

In another embodiment of the invention, provided is a method wherein said composition suppresses an allo-immune response in said organ.

In another embodiment of the invention, provided is a method said immunosuppressive agent comprises a mammalian target of rapamycin inhibitor, a calcineurin inhibitor or a combination thereof.

In another embodiment of the invention, provided is a method said immunosuppressive agent is rapamycin or a derivative thereof or combinations thereof.

In another embodiment of the invention, provided is a method the immunosuppressive agent comprises tacrolimus or a derivative thereof or combinations thereof.

In another embodiment of the invention, provided is a method the immunosuppressive agent comprises cyclosporin A or a derivative thereof or combinations thereof.

In another embodiment of the invention, provided is a method the immunosuppressive agent comprises a nuclear factor kappa-light-chain-enhancer of activated B cells (NFkB) inhibitor.

In another embodiment of the invention, provided is a method the immunosuppressive agent comprises a Janus kinase 3 (JAK3) inhibitor.

In another embodiment of the invention, provided is a method the immunosuppressive agent comprises Interleukin 2 (IL-2) R alpha or a derivative thereof or a combination thereof.

In another embodiment of the invention, provided is a method wherein the immunosuppressive agent comprises Complement C siRNA.

In another embodiment of the present invention, provided is a method wherein said immunosuppressive agent is encapsulated in a micelle In another embodiment of the invention, provided is a method said nanoparticle encapsulating said immunosuppressive agent has a mean diameter of 5 nm to 100 nm.

In another embodiment of the invention, provided is a method said nanoparticle encapsulating said immunosuppressive agent has a mean diameter of 10 nm to 15 nm.

In another embodiment of the invention, provided is a method said nanoparticle is pH sensitive, temperature sensitive or combinations thereof.

In another embodiment of the invention, provided is a method the micelle comprises N-palmitoyl homocysteine.

In another embodiment of the invention, provided is a method the micelle comprises amino-polyethylene glycol-phosphatidylethanolamine.

In another embodiment of the invention, provided is a method said targeting moiety is a peptide or peptidomimetic that binds Complement component 3 (C3) breakdown products and reperfusion epitopes, a peptide or peptidomimetic that binds an integrin, or combinations thereof.

In another embodiment of the invention, provided is a method said targeting moiety comprises the amino acid sequence Arg-Gly-Asp.

In another embodiment of the invention, provided is a method said targeting moiety comprises a cyclized Arg-Gly-Asp peptide or peptidomimetic.

In another embodiment of the invention, provided is a method said preservation solution is selected from the group consisting of Belzer UW Cold Storage Solution, Viaspan, CoStorSol, Kyoto ET Solution, Celsior Solution, Phosphate Buffered Sucrose Solution, Bretschneider Histidine Tryptophan Ketoglutarate (HTK) Solution, Ross-Marshall Citrate Solution, Euro-Collins Solutions and Perferdex.

In a further embodiment of the present invention, provided is a kit for producing a formulation to pre-treat an organ prior to transplantation, said kit comprising:

a) a first composition comprising a therapeutically effective amount of an immunosuppressive agent encapsulated in a micelle, liposome or polymeric nanoparticle that comprises on its surface a targeting moiety; and b) a second composition comprising a preservation solution.

In another embodiment of the present invention, provided is a kit further comprising instructions for use.

In a further embodiment of the present invention, provided is a method for suppressing or preventing an immune response or organ transplant rejection in a patient in need thereof, comprising the step of pre-treating an organ prior to transplantation comprising the step of administering to said organ a therapeutically effective amount of a formulation comprising a first composition comprising a therapeutically effective amount of an immunosuppressive agent encapsulated in a micelle, liposome or polymeric nanoparticle that comprises on its surface a targeting moiety; and a second composition comprising a preservation solution.

Drug Carrier Design and Targeting Moieties

In one embodiment of the present invention, and in order to design an efficient and effective drug carrier, a nanocarrier was designed with:

(1) a tailored surface to attach biomolecules for targeted drug delivery; (2) a biocompatible coating, which can efficiently encapsulate the hydrophobic drug thereby reducing cytotoxicity; and optionally (3) stimuli-induced disruption of the carrier for controlled drug release in the desired environment. Micelles or liposomes are a good choice of carrier as they fulfill these requirements based on their composition. The mono-targeted micelle-immunosuppressive agent conjugate delivery system has advantages, which derive from the physical and chemical protection offered to the conjugate by micelle encapsulation of the drug during its delivery to the transplantation site and release of the drug by micelle breakdown when it is in the immediate vicinity of the organ allograft.

The carrier includes a targeting moiety. In an embodiment of the invention, the targeting moiety is a peptide or peptidomimetic that binds Complement component 3 (C3) breakdown products and reperfusion epitopes, a peptide or peptidomimetic that binds an integrin, or combinations thereof. C3 breakdown products have been shown to deposit in cardiac allografts early post-transplantation as a response to ischemia-reperfusion injury, an unavoidable event in all solid organ transplants. By targeting C3 breakdown products, immunosuppressive agents (e.g., mTOR inhibitors such as rapamycin) can be delivered directly to the grafted organ.

C3 activation fragments are abundant complement opsonins found at a site of complement activation, and they serve as ligands for various C3 receptors. One such receptor, Complement Receptor 2 (CR2), a transmembrane protein, plays an important role in humoral immunity by way of its expression predominantly on mature B cells and follicular dendritic cells. CR2 is a member of the C3 binding protein family and consists of 15-16 short consensus repeat (SCR) domains, structural units that are characteristic of these proteins, with the C3 binding site being contained in the two N-terminal SCRs. Natural ligands for CR2 are iC3b, C3dg and C3d, cell-bound breakdown fragments of C3b that bind to the two N-terminal SCR domains of CR2. Cleavage of C3 results initially in the generation and deposition of C3b on the activating cell surface. The C3b fragment is involved in the generation of enzymatic complexes that amplify the complement cascade. On a cell surface, C3b is rapidly converted to inactive iC3b, particularly when deposited on a host surface containing regulators of complement activation. Even in absence of membrane bound complement regulators, substantial levels of iC3b are formed. iC3b is subsequently digested to the membrane bound fragments C3dg and then C3d by serum proteases, but this process is relatively slow. Thus, the C3 ligands for CR2 are relatively long lived once they are generated and will be present in high concentrations at sites of complement activation.

CR2 consists of an extracellular portion consisting of 15 or 16 repeating units known as short consensus repeats (SCRs). Amino acids 1-20 comprise the leader peptide, amino acids 23-82 comprise SCR1, amino acids 91-146 comprise SCR2, amino acids 154-210 comprise SCR3, amino acids 215-271 comprise SCR4. The active site (C3dg binding site) is located in SCR 1-2 (the first 2 N-terminal SCRs). SCR units are separated by short sequences of variable length that serve as spacers. It is understood that any number of SCRs containing the active site can be used. In one embodiment, the construct contains the 4 N-terminal SCR units. In another embodiment, the construct includes the first two N-terminal SCRs. In another embodiment the construct includes the first three N-terminal SCRs. An amino acid sequence for human CR2 is known in the art and found in Accession No. NM_001006658.

It is understood that species and strain variation exist for the disclosed peptides, polypeptides, proteins, protein fragments and compositions. Specifically disclosed are all species and strain variations for the disclosed peptides, polypeptides, proteins, protein fragments and compositions.

Also disclosed are compositions, wherein the construct is a fusion protein, Herein a "fusion protein" means two or more components comprising peptides, polypeptides, or proteins operably linked. CR2 can be linked to complement inhibitors or activators by an amino acid linking sequence. Examples of linkers are well known in the art. Examples of linkers can include but are not limited to (Gly4Ser)3 (SEQ ID NO: 1) (G4S) (SEQ ID NO: 2), (Gly3Ser)4 (SEQ ID NO: 3) (G3S) (SEQ ID NO: 4), SerGly4 (SEQ ID NO: 5), and SerGly4SerGly4 (SEQ ID NO: 6). Linking sequences can also consist of "natural" linking sequences found between SCR units within human (or mouse) proteins, for example VSVFPLE (SEQ ID NO: 7), the linking sequence between SCR 2 and 3 of human CR2. Fusion proteins can also be constructed without linking sequences.

In some embodiments, the agent that binds C3 breakdown products is coupled to a complement inhibitor. There are two broad classes of membrane complement inhibitor; inhibitors of the complement activation pathway (inhibit C3 convertase formation), and inhibitors of the terminal complement pathway (inhibit MAC formation). Membrane inhibitors of complement activation include Complement Receptor 1 (CR1), decay-accelerating factor (DAF) and membrane cofactor protein (MCP). They all have a protein structure that consists of varying numbers of repeating units of about 60-70 amino acids termed short consensus repeats (SCR) that are a common feature of C3/C4 binding proteins. Rodent homologues of human complement activation inhibitors have been identified. The rodent protein Crry is a widely distributed inhibitor of complement activation that functions similar to both DAF and MCP. Rodents also express DAF and MCP, although Crry appears to be functionally the most important regulator of complement activation in rodents. Although there is no homolog of Crry found in humans, the study of Crry and its use in animal models is clinically relevant.

Control of the terminal complement pathway and MAC formation in host cell membranes occurs principally through the activity of CD59, a widely distributed 20 kD glycoprotein attached to plasma membranes by a glucosylphosphatidylinositol (GPI) anchor. CD59 binds to C8 and C9 in the assembling MAC and prevents membrane insertion.

Various types of complement inhibitory proteins are currently under investigation for therapy of inflammatory disease and disease states associated with bio-incompatibility. Two of the best therapeutically characterized inhibitors of human complement are a soluble form of Complement Receptor 1 (sCR1) and an anti-05 monoclonal antibody. These systemically active inhibitory proteins have shown efficacy in various animal models of disease and more recently in clinical trials. Anti-05 mAb inhibits the generation of C5a and the MAC, whereas sCR1 is an inhibitor of complement activation and also inhibits the generation of C3 activation products. Soluble forms of human DAF and MCP, membrane inhibitors of complement activation, have also been shown to be protective an animal models of inflammation and bio-incompatability. CD59 is a membrane inhibitor of complement that blocks assembly of the MAC, but does not affect generation of complement opsonins or C3a and C5a. Soluble forms of CD59 have been produced, but its low functional activity in vitro, particularly in the presence of serum, indicates that sCD59 will have little or no therapeutic efficacy.

Constructs containing CR2 linked to complement inhibitors are described in U.S. Pat. No. 8,007,804 to Tomlinson et al., and U.S. Pat. No. 8,540,997 to Tomlinson et al., which are hereby incorporated by references in their entirety for the teaching of these constructs. In some embodiments, the surface agent comprises a peptide or peptidomimetic that binds an integrin. For example, a polypeptide comprising the amino acid sequence Arg-Gly-Asp (RGD) is capable of binding integrins. As used herein, the term "RDG sequence", "RGD peptide", or "RGD compound" means a molecule having at least one Arg-Gly-Asp sequence that functions to bind an integrin molecule, such as avr33. As used herein, the term "cyclic RGD sequence" or "cylcic RGD molecule" means a cyclic sequence or molecule comprising an "RGD sequence" as defined above.

Integrin receptors can bind a variety of RGD sequences of variety lengths (see, for example, Ruoslahti et al., In Morphoregulatory Molecules, G.M.Edelman et al., eds. (1990); Ruoslahti, J. Chin. Invest. 87:1-5 (1991)). Thus, it is intended that the length of an RGD peptide can vary, for example, from four amino acids up to 100 amino acids or more. For example, the RGD peptide can be from about 5 to about 50 amino acids, such as from about 6 to about 25 amino acids. Moreover, it is recognized that the amino acids or other entities that flank the RGD sequence can vary without destroying activity of the molecule. As such, variation of flanking amino acids are specifically contemplated, so long as the variant does not completely lose its activity.

Additionally, it is intended that the RGD sequence includes any compound having an amino acid sequence that is functionally equivalent to the sequence Arg-Gly-Asp. For example, one skilled in the art will recognize that substitution of amino acids can be made using non-natural or synthetic amino acids that result in a peptide having similar or equivalent functionality. Other examples of functional RGD equivalents include amino acid derivatives and mimics described, for example, in U.S. Pat. Nos. 5,612,311 and 5,858,972, which are incorporated herein by reference.

The RGD peptide can be linear or cyclic. In some embodiments, the surface agent comprises a cyclized arginine-glycineaspartic acid (cRGD). Cyclic or conformationally constrained RGD molecules are described, for example, in U.S. Pat. Nos. 5,547,936; 5,827,821; 5,672,585; 5,627,263 and 5,912,234, which are incorporated herein by reference. Such cyclic RGD molecules having disulfide linkages or other intramolecular bonds in various positions relative to the RGD motif can be used.

The nanocarrier can be any suitable vehicle for the delivery of active agents, including non-targeting and targeting. A variety of suitable nanocarriers are known in the art, and include for example micelles, solid nanoparticles, and liposomes.

In some embodiments, the nanocarrier can include a polymeric nanoparticle. For example, the nanocarrier can comprise one or more polymeric matrices. The nanocarrier can also include other nanomaterials and can be, for example, lipid-polymer nanoparticles. In some embodiments, a polymeric matrix can be surrounded by a coating layer (e.g., liposome, lipid monolayer, micelle, etc.). Examples of classes of nanocarriers that can be adapted (e.g., by incorporation of a suitable surface agent) to deliver immunosuppressive agents include (1) biodegradable nanoparticles, such as those described in U.S. Pat. No. 5,543,158 to Gref et al., (2) polymeric nanoparticles such as those described in U.S. Pat. No. 7,534,448 to Saltzman et al., (3) lithographically constructed nanoparticles, such as those described in U.S. Pat. No. 8,420,124 to DeSimone et al., (4) nanoparticles such as those described in U.S. Patent Application Publication No. 2010/0233251 to von Andrian et al., or (5) nanoparticles such as those described in U.S. Pat. No. 7,364,919 to Penades et al.

In some cases, release of the immunosuppressive agent (e.g., an mTOR inhibitor such as rapamycin or a derivative thereof) is triggered by the decrease in endosomal pH initiated by cellular uptake. The encapsulated immunosuppressive agent is then delivered at the level of the graft. Recent data suggests that rapamycin may impede the emigration of passenger leukocytes to lymphoid organs, confirming that the release of rapamycin at the level of the organ itself may blunt allo-immune responses. Accordingly, in some embodiments, the nanocarrier can be a nanocarrier which is pH sensitive so as to provide for the pH triggered release of the immunosuppressive agent. The term "pH triggered release" is intended to mean that the rate of release of the immunosuppressive agent from the nanocarrier is dependent on or regulated by the pH of the media or environment surrounding the nanocarrier.

For example, the nanocarrier can be a micelle or liposome that comprises N-palmitoyl homocysteine (PHC). Other pH sensitive lipids include N-(4-carboxybenzyl)-N,N-dimethyl-2,3-bis(oleoyloxy)propan-1-aminium (DOBAQ) and 1,2-dipalmitoyl-sn-glycero-3-succinate (DGS). These lipids can be used instead of PHC (N-palmitoyl homocysteine) in combination with PEG-PE amine. These molecules are zwitterionic in nature and are affected by pH changes of cellular milieu. In some embodiments, liposome can be created with a mPEG-Hz-CHEMS. mPEG-Hz-CHEMS has a pH sensitive hydrazone linkage which breaks at around endosomal pH (approximately pH5.5).

pH sensitive nanocarriers are known in the art. See, for example, U.S. Patent Application Publication No. 2004/0234597 to Shefer et al. and U.S. Patent Application Publication No. 2010/0303850 to Lipford et al. Suitable pH sensitive nanocarriers can be formed from materials that are pH sensitive provided that the resulting nanocarriers provide for delivery of the immunosuppressive agent at the desired pH. For example, suitable pH sensitive nanocarriers include nanocarriers that provide for the release of one or more encapsulated immunosuppressive agents at a threshold pH of about 6.8 or less (e.g., about 6.5 or less, about 6 or less, or about 5.5 or less).

Such synthetic nanocarriers are well known in the art and include polyketal nanocarriers, pH sensitive liposomes, pH sensitive micelles, polymeric nanoparticles derived from amphiphilic block copolymers, and core-shell materials formed from a core material (e.g., a hydrophobic or hydrophilic core material such as a polymer) and a pH sensitive shell (see for example, U.S. Patent Application Publication No. 2004/0234597 to Shefer et al.). In some embodiments, the pH sensitive nanocarrier can be a core-shell nanoparticle comprising a hydrophobic core material (e.g., a wax, a fat material such as a lipid, or a hydrophobic polymer) surrounded by a pH sensitive shell material.

In some embodiments, the pH sensitive nanocarrier can be a nanoparticle or micelle formed from an amphiphilic material, such as an amphiphilic block copolymer derived from a hydrophilic polymer segment and a hydrophobic polymer segment. By way of example, the pH sensitive nanocarrier can be a nanoparticle or micelle formed an amphiphilic block copolymer derived from a poly(alkylene oxide) segment (e.g., a polyethylene glycol (PEG) segment) and an aliphatic polyester segment. The aliphatic polyester segment can be a biodegradable aliphatic polyester, such as poly(lactic acid), poly(glycolic acid), or poly(lactic acid-co-glycolic acid).

In some embodiments, the pH sensitive nanocarrier can be a nanoparticle or micelle or liposome formed from amphiphilic molecule comprising a hydrophilic polymer segment (e.g., a poly(alkylene oxide) segment such as a PEG segment) and a lipid moiety. The lipid moiety can be conjugated to a terminus of the PEG segment, so as to afford a suitable amphiphile. Suitable lipid moieties are known in the art, and include, for example, mono-, di and triglycerides (e.g., glyceryl monostearate or glyceryl tristearate), phospholipids, sphingolipids, cholesterol and steroid derivatives, terpenes and vitamins.

In some embodiments, the lipid moiety can be a phospholipid. Suitable phospholipids include, but are not limited to, phosphatidic acids, phosphatidylcholines with both saturated and unsaturated lipids, phosphatidyl ethanolamines, phosphatidylglycerols, phosphatidylserines, phosphatidylinositols, lysophosphatidyl derivatives, cardiolipin, and beta-acyl-y-alkyl phospholipids. In certain embodiments, the pH sensitive nanocarrier can be a nanoparticle or micelle formed from amphiphilic molecule comprising a hydrophilic polymer segment (e.g., a poly(alkylene oxide) segment such as a PEG segment) and a phospholipid moiety.

In some embodiments, the targeted nanocarrier has a mean diameter of 1 nm to 100 nm to optimize vascular permeability and penetration into tissue and cells. In addition with its multifunctional character (large surface area due to small size, surface can be tailored with different functionalities), the nanocarrier behaves like a stealth agent and can evade immune response from the host system due to surface modifications including pegylation.

In some embodiments, the nanocarrier is conjugated with a near-infrared fluorophore, such as DyLight 680, Dylight 755, or IR-800. These fluorophores aid in noninvasive in vivo imaging for the detection of the graft site and monitoring of drug release. In some embodiments, the imaging reporter can be gadolinium, iron oxide, or radioisotopes to monitor delivery of the nanocarrier. In some embodiments, the imaging reporter is an enzyme, such as luciferase or beta-galactosidase.

Nanocarriers can include one or more immunosuppressive agents Immunosuppressive agents are agents that inhibit, slow, or reverse the activity of the immune system. Immunosuppressive agents act by suppressing the function of responding immune cells (including, for example, T cells), directly (e.g., by acting on the immune cell) or indirectly (by acting on other mediating cells), immunosuppressive agents can be given to a subject to prevent the subject's immune system from mounting an immune response after an organ transplant or for treating a disease that is caused by an overactive immune system.

Examples of Immunosuppressive Agents

Immunosuppressive agents useful for the present invention include, for example, calcineurin inhibitors (e.g., cyclosporin (CsA) and derivatives thereof; ISA(TX) 247, and tacrolimus(FK-506) and derivatives thereof); azathioprine (AZ); mycophenolate mofetil (MMF); mizoribine (MZ); leflunomide (LEF); adrenocortical steroids (also known as adrenocortical hormones, corticosteroids, or corticoids) such as prednisolone and methylprednisolone; sirolimus (also known as rapamycin); everolimus; FK778; TAFA-93; deoxyspergualin (DSG); FTY720 (chemical name: 2-amino-242-(4-octylphenyl)ethyl]-1,3-propanediol hydrochloride); cyclophosphamide; 15-deoxyspergualin (Gusperimus); interferons; sulfasalazine; mimoribine, misoprostol, anti-IL-2 receptor antibodies, thalidomide, antitumor necrosis factor antibodies, anti-CD2 antibodies, anti-CD-147 antibodies, anti-CD4 antibodies, anti-CD8 antibodies, anti-thymocyte globulin antibodies, interleukin-2 a-chain blockers (e.g., basiliximab and daclizumab); inhibitors of inosine monophosphate dehydrogenase (e.g., mycophenolate mofetil); and inhibitors of dihydrofolic acid reductase (e.g., methotrexate). In some cases, the immunosuppressive agent can include one or more calcineurin inhibitors. Calcineurin inhibitors include drugs or compounds that result in inhibition or down regulation of the biological activity associated with the calcineurin, or of the calcineurin-NFATc pathway, the calcineurin-cofilin pathway or the calcineurin-BAD pathway. Calcineurin inhibitors are known in the art, and include, for example, cyclosporines including cyclosporine A (CsA) and derivatives thereof such as voclosporin (ISA 247), and tacrolimus (FK-506) and derivatives thereof such as pimecrolimus.

In certain embodiments, the immunosuppressive agent can include a cyclosporine. Cyclosporines are fungal metabolites that comprise a class of cyclic oligopeptides that act as immunosuppressants. Cyclosporine A is a hydrophobic cyclic polypeptide consisting of eleven amino acids. It binds and forms a complex with the intracellular receptor cyclophilin. The cyclosporine/cyclophilin complex binds to and inhibits calcineurin, a $Ca^{2+}$-calmodulin-dependent serine-threonine-specific protein phosphatase. Calcineurin mediates signal transduction events required for T-cell activation. Cyclosporines and their functional and structural derivatives suppress the T cell-dependent immune response by inhibiting antigen-triggered signal transduction. This inhibition decreases the expression of proinflammatory cytokines, such as IL-2. Cyclosporines are highly hydrophobic and readily precipitate in the presence of water (e.g. on contact with body fluids).

Many different cyclosporines (e.g., cyclosporine A, B, C, D, E, F, G, H, and I) are produced by fungi. Cyclosporine A is commercially available under the trade name NEORAL® from Novartis. Cyclosporine A structural and functional derivatives include cyclosporines having one or more fluorinated amino acids (described, e.g., in U.S. Pat. No. 5,227,467); cyclosporines having modified amino acids (described, e.g., in U.S. Pat. Nos. 5,122,511 and 4,798,823); and deuterated cyclosporines, such as ISAtx247 (described in U.S. Patent Application Publication No. 2002/0132763 A1).

Additional cyclosporine derivatives are described in U.S. Pat. Nos. 6,136,357, 4,384,996, 5,284,826, and 5,709,797. Cyclosporine derivatives include, but are not limited to, D-Sar (a-SMe)3 Val2-DH-Cs (209-825), Allo-Thr-2-Cs, Norvaline-2-Cs, D-Ala(3-acetylamino)-8-Cs, Thr-2-Cs, and D-MeSer-3-Cs, D-Ser(O—$CH_2CH_2$—OH)-8-Cs, and D-Ser-8-Cs, which are described in Cruz et al. (Antimicrob. Agents Chemother. 44: 143-149, 2000).

In some embodiments, the immunosuppressive agent includes cyclosporine A. In some embodiments, the immunosuppressive agent includes a derivative of cyclosporine A, such as voclosporin.

In certain embodiments, the immunosuppressive agent can include tacrolimus or a derivative thereof. Tacrolimus (FK506 or Fujimycin) is an immunosuppressive agent that targets T cell intracellular signal transduction pathways. Tacrolimus binds to an intracellular protein FK506 binding protein (FKBP-12) that is not structurally related to cyclophilin. The FKBP/FK506 complex binds to calcineurin and inhibits calcineurin's phosphatase activity. This inhibition prevents the dephosphorylation and nuclear translocation of nuclear factor of activated T cells (NFAT), a nuclear component that initiates gene transcription required for proinflammatory cytokine (e.g., IL-2, gamma interferon) production and T cell activation. Thus, tacrolimus inhibits T cell activation.

Tacrolimus derivatives are known in the art, and are described, for example, in U.S. Pat. Nos. 4,894,366, 4,929,611, and 4,956,352. By way of example, FK506-related compounds, including ascomycin (FR-900520), FR-900523, and FR-900525, are described in U.S. Pat. No. 5,254,562; O-aryl, O-alkyl, O-alkenyl, and O-alkynyl macrolides are described in U.S. Pat. Nos. 5,250,678, 532,248, 5,693,648; amino O-aryl macrolides are described in U.S. Pat. No. 5,262,533; alkylidene macrolides are described in U.S. Pat. No. 5,284,840; N-heteroaryl, N-alkylheteroaryl, N-alkenylheteroaryl, and N-alkynylheteroaryl macrolides are described in U.S. Pat. No. 5,208,241; aminomacrolides and derivatives thereof are described in U.S. Pat. No. 5,208,228; fluoromacrolides are described in U.S. Pat. No. 5,189,042; amino O-alkyl, O-alkenyl, and O-alkynylmacrolides are described in U.S. Pat. No. 5,162,334; and halomacrolides are described in U.S. Pat. No. 5,143,918. Pimecrolimus, another tacrolimus derivative, is a 33-epi-chloro derivative of ascomyin. Pimecrolimus structural and functional derivatives are described, for example, in U.S. Pat. No. 6,384,073. In some embodiments, the immunosuppressive agent includes ascomycin.

In some cases, the immunosuppressive agent can include one or more mTOR inhibitors. mTOR inhibitors include compounds or ligands, or pharmaceutically acceptable salts thereof, which inhibit cell replication by blocking the progression of the cell cycle from G1 to S through the modulation of mTOR activity or expression. A number of mTOR inhibitors are commercially available or under development, including rapamycin (sirolimus, marketed under the trade name RAPAMUNE® by Wyeth), temsirolimus (TORISEL®; Wyeth), everolimus (also known as RAD001; marketed under the trade names ZORTRESS® and AFINITOR® by Novartis), ridaforolimus (also known as deforolimus, AP23573, and MK-8669, being developed by Merck and ARIAD pharmaceuticals), TOP216 (Toptarget A/S), OSI-027 (OSI Pharma), TAFA93 (Isotechnika), nab-rapamycin (APP Phama), and merilimus.

In some embodiments, the pharmaceutical composition contains rapamycin (sirolimus, marketed under the trade name RAPAMUNEO by Wyeth), Rapamycin is a macrolide produced by *Streptomyces hygroscopicus*. Rapamycin is a potent immunosuppressive agent, and is used clinically to prevent rejection of transplanted organs. In some embodiments, the pharmaceutical composition contains a rapamycin derivative. Rapamycin derivatives include compounds that are chemically or biologically modified derivatives of the rapamycin nucleus which retain activity as mTOR inhibitors. Examples of rapamycin derivatives include esters, ethers, carbamates, oximes, hydrazones, and hydroxylamines of rapamycin, as well as compounds in which one or more of the functional groups attached to the attached to the rapamycin nucleus have been modified, for example, through reduction or oxidation.

Suitable rapamycin derivatives include rapamycin derivatives containing a substitution at the C-40 position of rapamycin. If the C-40 substituent is designated as R, then the following substitutions and corresponding suitable compounds are: R=—OP(O)(Me)$_2$, AP23573 (International Patent Publication Nos. WO 98/02441 and WO 2001/14387); R=OC(O)C(CH$_3$)(CH$_2$OH), temsirolimus (U.S. Pat. No. 5,362,718); R=—OCH2CH2OH, everolimus (U.S. Pat. No. 5,665,772); R=—OCH2CH2OEt, biolimus; R=-tetrazole, zotarolimus or ABT-578 (International Patent Publication No. WO 99/15530); and R=—Cl, pimecrolimus.

Other suitable rapamycin derivatives include those having substitutions in the C-40 and/or C-16 and/or C-32 positions. Esters and ethers of rapamycin are described in the following patents, which are all hereby incorporated by reference: alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. Nos. 5,118,678; 5,411,967; 5,434,260; 5,480,988; 5,480,989; 5,489,680); silyl esters (U.S. Pat. No. 5,120,842); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258, 389); carbonate esters (U.S. Pat. No. 5,260,300); arylcarbonyl and alkoxycarbonyl carbamates (U.S. Pat. No. 5,262,423); carbamates (U.S. Pat. No. 5,302, 584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); amidinocarbamate esters (U.S. Pat. No.5,463,048); hindered N-oxide esters (U.S. Pat. No. 5,491,231); biotin esters (U.S. Pat. No.5,504,091); O-alkyl ethers (U.S. Pat. No. 5,665, 772); and PEG esters of rapamycin (U.S. Pat. No. 5,780, 462); 32-esters and ethers (U.S. Pat. No. 5,256,790). Other suitable rapamycin derivatives include oximes, hydrazones, and hydroxylamines of rapamycin as disclosed in U.S. Pat. Nos. 5,373,014, 5,378,836, 5,023,264, and 5,563,145, 40-oxorapamycin, another suitable rapamycin derivative, is disclosed in U.S. Pat. No. 5,023,263.

In certain embodiments, the immunosuppressive agent includes everolimus, temsirolimus, biolimus, zotarolimus, ridaforolimus.

Other suitable immunosuppressive agents include small molecule inhibitors of mTOR, including fused bicyclic compounds (such as those described in International Patent Publication Nos. WO 2007/61737, WO 2007/87395, WO 2007/64993, and U.S. Patent Application Publication No. US 2007/0112005), heteroaromatic amines (such as those described in International Patent Publication No. WO 2001/19828), pyrrolopyrimidine compounds (such as those described in International Patent Publication No. WO 2005/47289), diphenyl-dihydro-indol-2-one derivatives (such as those described in International Patent Publication No. WO 2005/97107), and trimethydodeca-triene derivatives (such as those described in US Patent Publication No. 2007/037887). Also suitable are dual PI3K/mTOR kinase inhibitors, such as the compound PI-103, as described in Fan, Q-W, et al. *Cancer Cell* 9:341-349 (2006) and Knight, Z. A. et al. *Cell* 125:733-747 (2006).

The immunosuppressive agent can also be a pharmaceutically acceptable prodrug of an immunosuppressive agent, for example a prodrug of an mTOR inhibitor such as rapamycin or a rapamycin derivative. Prodrugs are compounds that, when metabolized in vivo, undergo conversion to compounds having the desired pharmacological activity (e g , immunosuppressive activity). Prodrugs can be prepared by replacing appropriate functionalities present in immunosuppressive agent with "pro-moieties" as described, for example, in H. Bundgaar, Design of Prodrugs (1985). Examples of prodrugs include ester, ether or amide derivatives of the immunosuppressive agents described herein, and their pharmaceutically acceptable salts. For further discussions of prodrugs, see, for example, T. Higuchi and V. Stella "Pro-drugs as Novel Delivery Systems," ACS Symposium Series 14 (1975) and E. B. Roche ed., Bioreversible Carriers in Drug Design (1987).

The immunosuppressive agent can also be a pharmaceutically acceptable salt of an immunosuppressive agent, such as a salt of an mTOR inhibitor such as rapamycin or a rapamycin derivative. In some cases, it may be desirable to prepare a formulation containing a salt of an immunosuppressive agent due to one or more of the salt's advantageous physical properties, such as enhanced stability or a desirable solubility or dissolution profile. Generally, pharmaceutically acceptable salts of immunosuppressive agents can be prepared by reaction of the free acid or base forms of the immunosuppressive agent with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found, for example, in Remington's Pharmaceutical Sciences, 20th ed., Lippincott Williams & Wilkins, Baltimore, Md., 2000, p. 704.

Suitable pharmaceutically acceptable acid addition salts of immunosuppressive agent, when possible, include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, P-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

In some cases, the pharmaceutically acceptable salt of an immunosuppressive agent may include alkali metal salts, including but not limited to sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts. Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl (C1-C6) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

Formulations can also contain a pharmaceutically acceptable clathrate of an immunosuppressive agent, such as a clathrate of an mTOR inhibitor such as rapamycin or a rapamycin derivative. Clathrates are drug-host inclusion complexes formed when a drug is associated with or in a host molecule or molecules in stoichiometric ratio. For example, rapamycin or rapamycin derivatives can form inclusion complexes with cyclodextrins or other host molecules.

Many immunosuppressive agents, for example mTOR inhibitors such as rapamycin and derivatives of rapamycin, as well as pharmaceutically acceptable prodrugs or salts thereof, may contain one or more chiral centers, and thus exist as one or more stereoisomers. Such stereoisomers can be prepared and/or isolated as a single enantiomer, a mixture of diastereomers, or a racemic mixture. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

Formulation with Pre-Treatment Solution

The formulation of the invention to pre-treat an organ prior to transplantation can include a composition comprising a preservation solution. A skilled artisan would readily understand that any preservation solution currently in use can be used. Commonly used solutions include: University of Wisconsin (UW) solution, Belzer UW Cold Storage Solution, Viaspan, CoStorSol, Kyoto ET Solution, Celsior Solution, Phosphate Buffered Sucrose Solution, Bretschneider Histidine Tryptophan Ketoglutarate (HTK) Solution, Ross-Marshall Citrate Solution, Euro-Collins Solutions and Perferdex. Different solutions are used for different organs, such as Perfedex for the lung. In addition, different solutions are preferred at different institutions.

In one embodiment, University of Wisconsin (UW) solution, which was developed for liver, kidney, and pancreas preservations, can be used in the formulation of the present invention. UW solution is considered the standard for renal, pancreas, and hepatic preservation, effectively extending the ischemic time for kidneys, pancreas and livers and allowing them to be transported considerable distances to waiting recipients. The composition of the solution is complex. The solution has an osmolality of 320 mmol $kg^{-1}$ and pH 7.4 at room temperature and is composed of the following: Potassium 135 mmol $L^{-1}$, Sodium 35 mmol $L^{-1}$, Magnesium 5 mmol $L^{-1}$, Lactobionate 100 mmol $L^{-1}$, Phosphate 25 mmol $L^{-1}$, Sulphate 5 mmol $L^{-1}$, Raffinose 30 $mmol^{-1}$, Adenosine 5 mmol $L^{-1}$, Allopurinol 1 mmol $L^{-1}$, Glutathione 3 mmol $L^{-1}$, Insulin 100 U $L^{-1}$, Dexamethasone 8 mg $L^{-1}$, Hydroxyethyl starch (HES) 50 g $L^{-1}$, and Bactrim 0.5 ml $L^{-1}$. The components of UW solution, as with the other aforementioned solutions, are utilized to prevent cellular edema, cell destruction, maintain organ metabolic potential, and to maximize organ function after perfusion is reestablished. TRaM can be incorporated into preservation solutions at a concentration ranging from 100-2000 ng/ml.

Additional Components of Formulation for Administration

The disclosed targeted nanocarriers can be used therapeutically in combination with a pharmaceutically acceptable carrier. Pharmaceutical carriers are known to those skilled in the art. These most typically would be standard carriers for administration of drugs to humans, including solutions such as sterile water, saline, and buffered solutions at physiological pH. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The invention will now be further described in the Examples below, which are intended as an illustration only and do not limit the scope of the invention.

EXAMPLES

Reagents and Experimental Methods

Human Umbilical Vein Endothelial Cells (HUVEC), complete endothelial growth medium-2 (EGM-2) and bullet kit were purchased from Lonza (Walkersville, Md.). Cells were grown and maintained in a humidified 37° C. and 5% CO2 atmosphere. Cells were expanded on T75 $cm^2$ polystyrene flasks to passage 5 and plated onto 6-well plates for experimental assays (Fischer Scientific, Pittsburgh, Pa.). MCEC, a normal mouse cardiac endothelial cell line from Cedarlane (Ontario, Canada), were cultured in Dulbecco's Modified Eagle Medium (DMEM) (Life Technologies, CA) supplemented with 10% fetal bovine serum (FBS) in a 37° C. incubator with humidified room air and 5% $CO_2$.

Confocal microscopy. For visualization studies of cellular internalization of NPs, HUVEC were plated on 35 mm glass dishes (MatTek Corp., MA) and grown to confluence. NP solutions were prepared as described previously. Growth medium was replaced by NP solutions (10 or 100 ng $mL^{-1}$) or EGM-2 vehicle. Cells were incubated for either 6 or 24 hours. After incubation, cells were washed with EGM-2 and fixed with (4% w/w) paraformaldehyde (Affymetrix, CA) at room temperature for 5 minutes. Cellular internalization of the Dylight 680-conjugated NPs was visualized using an Olympus Fluoview FV10i LIV Confocal Microscope (Olympus, N.C.), 60x objective. Mean fluorescence intensity calculated and analyzed by ImageJ (NIH). All fluorescence intensities were normalized to vehicle control images.

Cell sorting. Spleens were surgically removed from mice and splenocytes were isolated via cell straining. CD90.2 Microbeads (Miltenyi Biotec, CA) were used along with an autoMACS Pro Separator (Miltenyi Biotec, CA) to isolate T-cells from splenocytes to >95% purity. T cells were then co-cultured (at 100,000 cells per well) with rapamycin or TraM pre-treated MCECs in 12 well plates at 4° C. in a hypoxic chamber.

Hypoxic cold storage cell culture model. A modified cell culture model that simulates the IR process of heart transplantation was used as previously described. (See W. Gao, J. Zhao, H. Kim, S. Xu, M. Chen, X. Bai, H. Toba, H. R. Cho, H. Zhang, S. Keshavjeel and M. Liu, *J Heart Lung Transplant*, 2014, 33, 309-315; and J. A. Cardella, S. Keshavjee, E. Mourgeon, S. D. Cassivi, S. Fischer, N. Isowa, A. Slutsky and M. Liu, *Journal of applied physiology*, 2000, 89, 1553-1560). Briefly, a confluent monolayer of MCECs underwent a period of simulated cold ischemia time (CIT) for 6 hours by replacing the DMEM containing 10% FBS with University of Wisconsin (UW; Bridge to Life, SC), a clinically used heart preservation solution, in a sealed hypoxic chamber filled with nitrogen at 4° C. After CIT, cells underwent 24 hours of simulated reperfusion by removing the preservation solution and reintroducing fresh DMEM containing 10% FBS, and then were incubated under normal culture conditions. To test the ability of free rapamycin and TraM to reduce cold storage and ischemia reperfusion-induced endothelial activation, EC were stored in UW with or without free rapamycin or TraM at 100 ng $ml^{-1}$. Efficacy was tested by measurement of supernatant mouse IL-8 (KC) by ELISA assay (BD Biosciences, CA) 24 hours post-reperfusion.

Animals. Animal experiments were performed according to Institutional Animal Care and Use Committee (IACUC) approved policies and guidelines at the Medical University of South Carolina (MUSC). The housing, feeding and care of animals used for these experiments were directed by veterinarians on staff at MUSC, trained and experienced in the proper care, handling and use of the mice. Research was conducted in compliance with the Animal Welfare Act and other federal statutes and regulations pertaining to animals and experiments involving animals, and adheres to principles stated in the Guide for the Care and Use of Laboratory Animals, NRC publication, 2011 edition.

Ex vivo fluorescence imaging. Mouse aortas were surgically removed and incubated with increasing concentrations of TraM, RaM, empty micelles or UW solution. The organs were imaged at 0, 6 and 24 hours. Fluorescent multispectral images were obtained using the Maestro In Vivo Imaging System (PerkinElmer, MA). Multispectral images were acquired under a constant exposure of 2000 ms with an orange filter acquisition setting of 630-850 nm in 2 nm increments. Multispectral images were unmixed into their component spectra (Dylight 680, autofluorescence, and background) and these component images were used to gain quantitative information in terms of average fluorescence intensity by creating regions of interest (ROIs) around the organs in the Dylight 680 component images.

Aortic Transplantation Model. Male Balb/c ($H-2^d$) and C57BL/6 (B6;$H-2^b$) mice (8-10 weeks) were obtained from Jackson laboratory (Bar Harbor, Me.). All mice weighed 25-30 g and were housed under specific pathogen-free conditions at the Medical University of South Carolina (Charleston, S.C.) and were used for transplantation studies. In the following series, transplants to male B6 mice were performed under clean conditions using Balb/c donors in the allograft group (Balb/c to B6, n=20) and B6 donors in the isograft group (B6 to B6, n=10). The mice were anesthetized with intraperitoneal injections of ketamine (75 mg/kg, Lloyd Laboratories, Shenandoah, Iowa, USA) and xylazine (16 mg/kg, Vedco, Inc., St. Joseph, Mo., USA) diluted in in sterile normal saline. An operating microscope with 16×magnification was used for the surgical procedure. The cuff used for the anastamosis consisted of a 0.6 mm body and a 0.6 mm extension crafted from a 24 gauge polyimide catheter (inner diameter 0.5 mm, wall thickness 0.025 mm, cat. No. 141-0027, Vention Medical, NH, USA). All procedures were approved by the Medical University of South Carolina Committee for Animal Research in accordance with the National Institutes of Health Guide for Care and Use of Laboratory Animals.

Donor Operation

After satisfactory anesthetic was administered, the donor mouse was placed in supine position and a midline thoraco-abdominal incision was made. 0.4 mL of saline containing 50 U of heparin (SAGENT Pharmaceuticals, IL, USA) was injected into the inferior vena cava as the initial step. For orthotopic transplantation, the bowel was reflected cephalad, the colon was retracted to the animal's left side, and the seminal vesicles and testes were distracted caudally. The segment of aorta between the left renal artery and its bifurcation was separated from inferior vena cava and harvested (FIG. 1a). For heterotopic transplantations, the left lung was reflected to the animal's right side across midline and the diaphragm was incised in order to achieve better exposure. The descending aorta and the intercostal arteries originating from descending aorta were isolated from surrounding tissues (FIG. 1b). All intercostal arteries were cauterized with a low-temperature adjustable fine tip cautery (Bovie Medical Corporation, FL, USA). The distal segment of descending aorta near the diaphragmatic hiatus was harvested and the aortic graft was placed on gauze and flushed free of remaining blood with saline. Once prepared, a 24-gauge cuff was fashioned for insertion into both ends of aortic graft. The cuff extension was handled with fine-tip forceps and the aorta was inserted inside the cuff and everted exposing the endothelial surface (FIG. 1c). The cuff was secured around the aorta with 10-0 nylon suture tie (ARO-Surgical Instruments corporation, Newport Beach, Calif.). The donor aorta was stored in ice-cold UW solution for further experimentation (Bridge to Life Ltd, SC, USA).

Recipient Operation

The recipient was placed in a supine position, with the tail facing the operator. A midline abdominal incision was performed from the xyphoid to pubic symphysis and a self-retaining retractor was placed to expose the abdominal contents. The intestine, wrapped in moistened sterile gauze, was gently reflected cephalad, the seminal vesicles and testis were covered and retracted caudally. The mesosigmoid was divided and a strip of sterile gauze was allowed to pass under the sigmoid colon, which was used to retract the sigmoid colon to the animal's left side (FIG. 2a). 0.2 mL of saline solution containing 25 U of heparin was injected into abdominal cavity. Using 2 super fine tip forceps and cautery, the retroperitoneal tissue surrounding the abdominal aorta and inferior vena cava (IVC) including the reproductive vessels were divided, which allowed for exposure of lumbar arteries and veins between the renal vessels and the iliac bifurcation. The lumbar vessels were cauterized and isolated from abdominal aorta and IVC (FIG. 2b), and lumbar arteries to the right were suture ligated below the right lumber vein (FIG. 2c). The infrarenal aorta between the left renal artery proximally and iliac bifurcation distally was dissected free and fully mobilized. The proximal and distal portions of the aorta were clamped by 2 stainless steel microserrefines (Fine Science Tools, CA, USA) (FIGS. 3a and 3b). A small incision was made at the proximal and distal ends of the aorta with vannas spring scissors (Fine Science Tools, CA, USA) and the arterial lumen was flushed with heparinized saline through the incisions. A suture was used to retract the lateral wall of the incised artery to the animal's left side (FIG. 3c). The opposite arterial sidewall was grasped with super fine tip forceps, and the cuffed end of donor aorta was inserted into recipient's proximal arterial lumen (FIG. 4a), and fixed by a circular ligature of 10-0 silk suture (FIG. 4b). The distal side of the cuffed end was inserted in a similar fashion (FIG. 4c). The curved donor aorta was lifted gently and the recipient's native aorta was resected (FIG. 5a). The entire abdominal aorta including the donor aorta was then straightened in line (FIG. 5b). The distal and proximal clamps were released in sequence, and pulsatile flow in the donor arterial segment was clearly visible (FIG. 5c). The abdominal contents were returned to the abdominal cavity, and the incision was closed with a running 4-0 silk suture.

Statistical analysis. All data is expressed as mean±SD. All data analysis was performed using GraphPad Prism software version 6 (La Jolla, Calif.) unless specified. Multiple variables were analyzed via analysis of variance techniques, p value<0.05 was considered statistically significant.

Example 1

Targeted Rapamycin Micelle Synthesis and Characterization

This example provides for the synthesis of nanocarrier constructs for in vitro analysis, Rapamycin Micelles (RaM) and Arginine-Glycine-Aspartate (cRGD) Targeted Rapamycin Micelles (TraM). These rapamycin containing micelles were synthesized using PEG-PE-amine and N-palmitoyl homocysteine (PHC) (FIG. 1a). Amine functionality on PEG-PE amine was utilized for further tailoring of the micelle with the targeting cyclic peptide arginine-glycine-aspartate (cRGD) moiety, and labeled with the fluorescent dye, Dylight 680, for tracking the micelle in in vitro cellular uptake studies. Results revealed that RaM are relatively monodisperse and measure at 9.8 nm±1.2 nm (PDI 0.1) in size (FIG. 1b). Conjugation of TraM with cRGD peptide shifts the size of the nanocarriers to approximately 15.3 nm±2.3 nm (PDI 0.03) in size. Using dynamic light scattering (DLS), size distribution was found to be identical to the instrumental response function corresponding to a monodispersed sample, indicating that aggregation is negligible. It is noteworthy that the hydrodynamic value is expected to be larger than the actual diameter because of the counter-ion cloud contributions to particle mobility. UV-Vis spectra (FIG. 1c) of RaM and TraM show rapamycin and Dylight 680 excitation at 270 nm and 680 nm, respectively, demonstrating encapsulation and conjugation, respectively, of both components. The concentration of the encapsulated rapamycin is calculated using UV-Vis spectroscopy; each batch is purified and concentrated for consistency.

In detail, micelle encapsulation of rapamycin (RaM) was carried out as described by Dubertret et al. (See B. Dubertret, P. Skourides, D. J. Norris, V. Noireaux, A. H. Brivanlou and A. Libchaber, *Science,* 2002, 298, 1759-1762). Rapamycin was mixed with 2.5 mg amino-PEG-PE (1,2-diacyl-sn-glycero-3-phosphoethanol-amine-N-[amino-poly(ethylene glycol)] and 0.5 mg PHC (N-palmitoyl homocysteine (ammonium salt)), suspended in 1 ml of chloroform. The chloroform mixture was sonicated for 30 minutes at room temperature in a water bath. The solvent was evaporated in a vacuum oven at room temperature for 3 hours. Lipids were purchased from Avanti Polar Lipids (AL). The pellet obtained after evaporation was heated to 80° C. and dissolved in nanopure water to produce amine-functionalized micelles. The micelle solution was sonicated for 1 hour in a water bath and filtered using a 0.2 μm syringe filter to remove aggregates. For the synthesis of TraM, the RaM solution was used for peptide conjugation (1:1 ratio of carboxyl group on peptide to amine group on the micelles at 30% coverage of amines). 10 μl of cRGD (1 mg per 200 μl in DMSO) was added to 1 ml of MES buffer (pH 4.5) in separate scintillation vials followed by 4 μl EDC and 11 μl sulfo-NHS (10 mg per 100 μl in MES). After 15 minutes of incubation at room temperature, PBS (pH~12) was added to bring the pH back to 7.5. The micelle solution was added to the peptide solution and incubated for 2 hours at room temperature. Excess peptide was removed using 10K MWCO ultracentrifugal device (Millipore, Md.) at 4000 rpm for 15 minutes at 4° C. For dye labeling, 1 μl of NHS Dylight 680 (1 mg per 200 μl in DMSO) was added at a ratio covering 30% amine groups of the micelles to RaM and TraM, respectively. The solution was incubated for 1 hour at room temperature. Excess dye was removed using 10K MWCO ultracentrifugal device at 4000 rpm for 15 minutes at 4° C.

Stability of the NPs was evaluated over a 24 hours period. To mimic the physiologic environment, the NPs were suspended in saline (phosphate buffered saline (PBS), pH 7.2) and drug absorbance monitored (FIG. 1d). Both constructs were relatively stable over the 24 hours and did not show any significant aggregation of the drug (loss of absorbance at 275 nm of ~20-26%). The stability of these NPs was also tested in serum since the presence of lipids, amino acids, and proteins in the serum could contribute to NP instability (FIG. 1e). The NPs were slightly more stable than those suspended in saline over the same period with overall loss of absorbance at 275 nm of ~14-18%. These NP stability experiments confirmed the robust nature of the NPs for potential use in in vivo studies.

Dynamic Light Scattering (DLS) of micelles in aqueous solution was performed on a ZetaPALS particle analyzer (Brookhaven Instruments, NY). The respective aqueous master solution was diluted and sonicated to prevent aggregation. The solution was filtered using a 0.2 μm syringe filter before taking the measurements. The concentrations of each micelle batch were determined by UV-Vis absorption using a Biotek microplate spectrophotometer (Winooski, Vt.). For pH change experiments, PBS buffers of pH 4-9 were prepared. RaM or TraM-cRGD ($\sim 10^{-4}$ M) were placed in a 96 well plate. PBS buffers of increasing pH were added to respective wells. The wells were incubated for 4 hours. After 4 hours, UV-Vis measurements were recorded at 275 nm (rapamycin absorbance).

Figure 2:
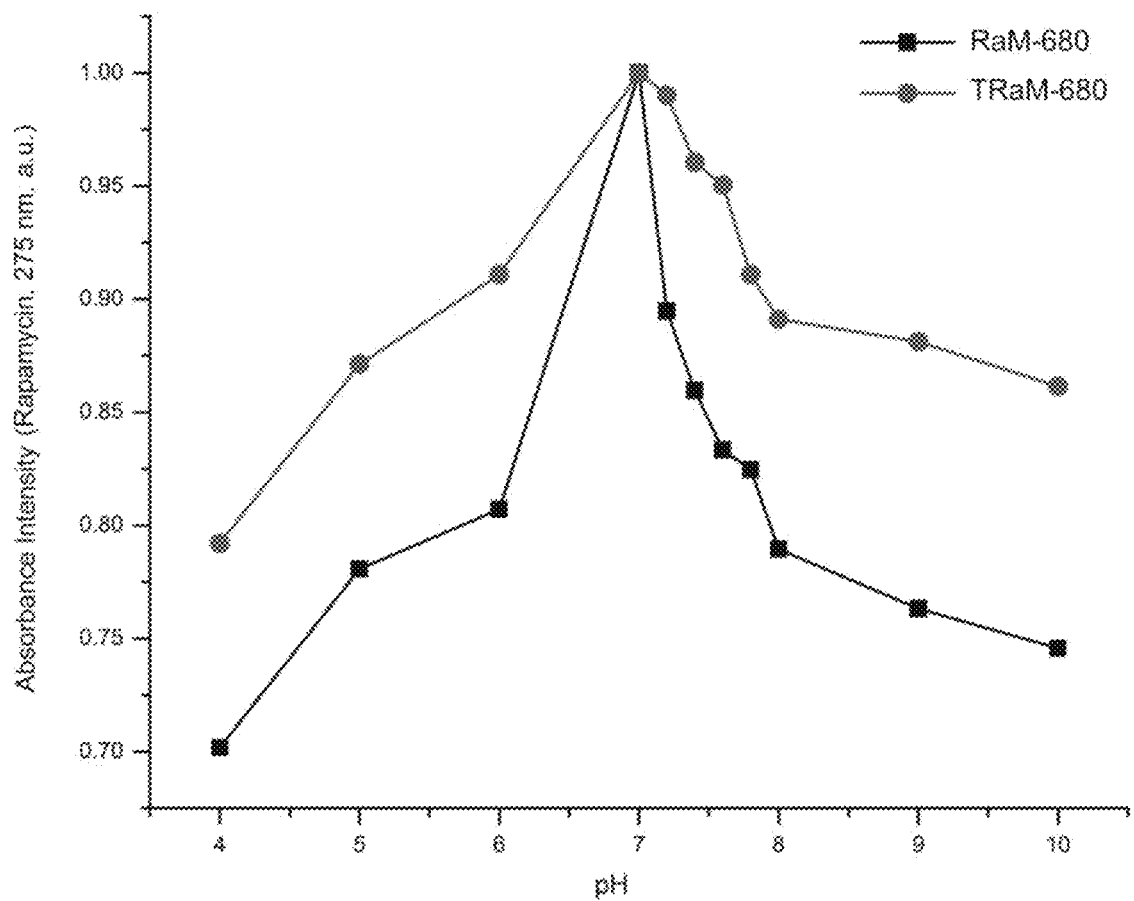
FIG. 2 shows the pH-dependent release of encapsulated rapamycin. Absorbance of rapamycin (275 nm)-filled NPs is high between pH 7 and 7.6 and is lost outside of the physiologic range due to NP rupture.

It was determined that rapamycin was encapsulated inside the hydrophobic micelle core, which reduced the interaction of the drug with the cellular environment. It was also observed that encapsulation can potentially decrease cytotoxicity of the drug and subsequent side effects of parenchymal absorption. However, once the drug is delivered it must be released from its micelle package. PHC is a pH sensitive lipid that when incorporated within a micelle ruptures at an approximate pH of 5.0. (See J. Connor and L. Huang, *The Journal of cell biology*, 1985, 101, 582-589; and D. Collins, F. Maxfield and L. Huang, *Biochimica et biophysica acta*, 1989, 987, 47-55). High absorbance of rapamycin is seen between a pH of 7.0 and 7.6 with less than 5% loss of fluorescence indicating that the TraM remains intact in this physiologic range (FIG. 2). In contrast, RaM undergoes a 17.5% rupture within the same range, suggesting that the cyclic targeting moiety (cRGD) imparts some benefit in preventing rupture. These results further suggest that the NPs hold the rapamycin inside its core and resist rupture at physiologic pH. At a pH lower than 7 and higher than 8, the fluorescence intensity significantly decreases indicating the rupture of the micelle due to the pH sensitive lipid composition. Rapamycin is released from the micelle and the hydrophobic drug quickly aggregates within the hydrophilic solvent. Upon rupture, the free drug is then removed from the optical path of the excitation wavelength.

In further detail, cells were plated at consistent densities of $1-2 \times 10^5$ cells per well and grown to confluence. A 1 mg $mL^{-1}$ stock solution of rapamycin (Sigma-Aldrich, WI) and dimethyl sulfoxide (DMSO) was prepared and stored at 4° C. The stock solution was used to prepare free rapamycin solutions and NPs as described previously. Targeted NPs, untargeted NPs, and free rapamycin were diluted in EGM-2 media to 10 and 100 ng $mL^{-1}$ concentrations. Cells were pre-incubated with 0.01% DMSO vehicle, EGM-2 media, free rapamycin, or NPs for 1 hour. Cells were washed two times with 0.02% Bovine Serum Albumin diluted in Hanks Balanced Salt Solution (HBSS/BSA wash solution). $H_2O_2$ (30% w/w; Sigma-Aldrich, MO) was diluted in HBSS/BSA wash solution (250 μM) and was applied immediately to designated wells. Following an 1 hour incubation, cells were washed with HBSS/BSA wash solution. Cells were then incubated in EGM-2 media for an additional 72 hours. Supernatants were then collected and cells were counted for further experimental analysis.

Example 2

Cellular Toxicity

Figure 3:
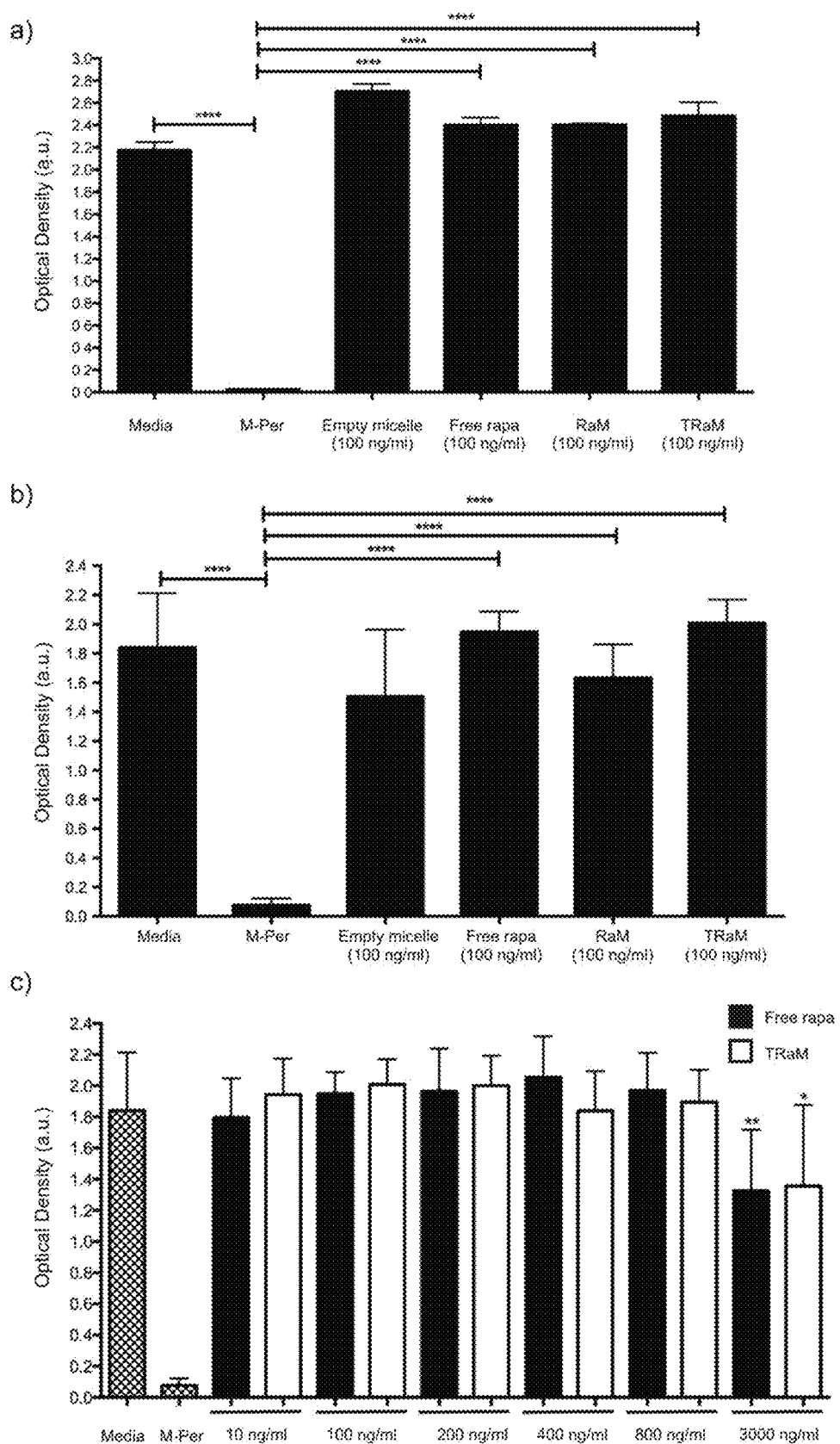
FIG. 3 shows TRaM impact on toxicity and cell viability. Standard MTS assays depicting the cell viability of a) HUVEC and b) MCEC cultured with a known toxic agent (M—per cell lysate), empty micelles, free drug, RaM, and TRaM for 6 hours. Treatment with empty micelle, free rapamycin, RaM or TRaM do not result in significant cell toxicity and death, c) MCEC cultured with increasing concentrations of free drug or TRaM do not show any significant cell death until 3000 ng ml$^{-1}$.
Figure 4:
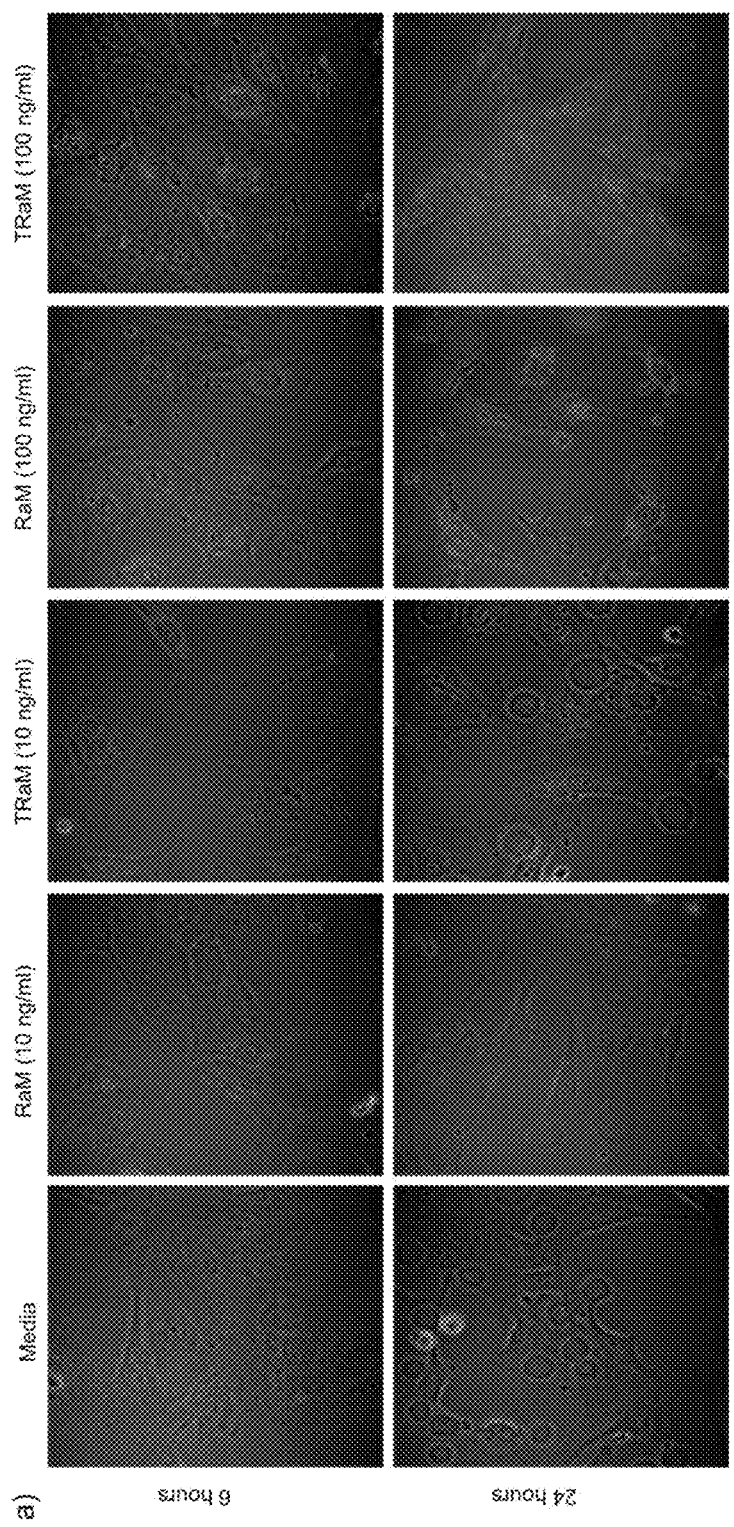
FIG. 4 shows the accumulation of TRaM into HUVECs. a) Confocal microscopy was performed to assess the uptake of RaM and TRaM (10 or 100 ng ml$^{-1}$) by HUVEC at 6 and 24 hours. RaM and TRaM (red) were taken up in a time-dependent fashion. TRaM appeared to internalize more rapidly than RaM, b) Mean fluorescence of internalized NPs at 24 hours was performed to quantify uptake. TRaM show a significant increase in intensity when compared to RaM and media control (***P<0.001), c) TRaM (red) accumulates in integrin αVβ3 (green) positive HUVEC after 24 hours. Nuclei stained with Hoechst stain (blue), d) HUVECs pre-incubated with (+BA) or without (-BA) brefeldin A were treated with TRaM (red) or RaM (black) for 1 hour and assessed for fluorescence accumulation (680 nm) within the cells over a 6 hours period. TRaM were rapidly internalized in the absence of BA. BA pre-treatment significantly reduced internalization of TRaM.
Figure 4:
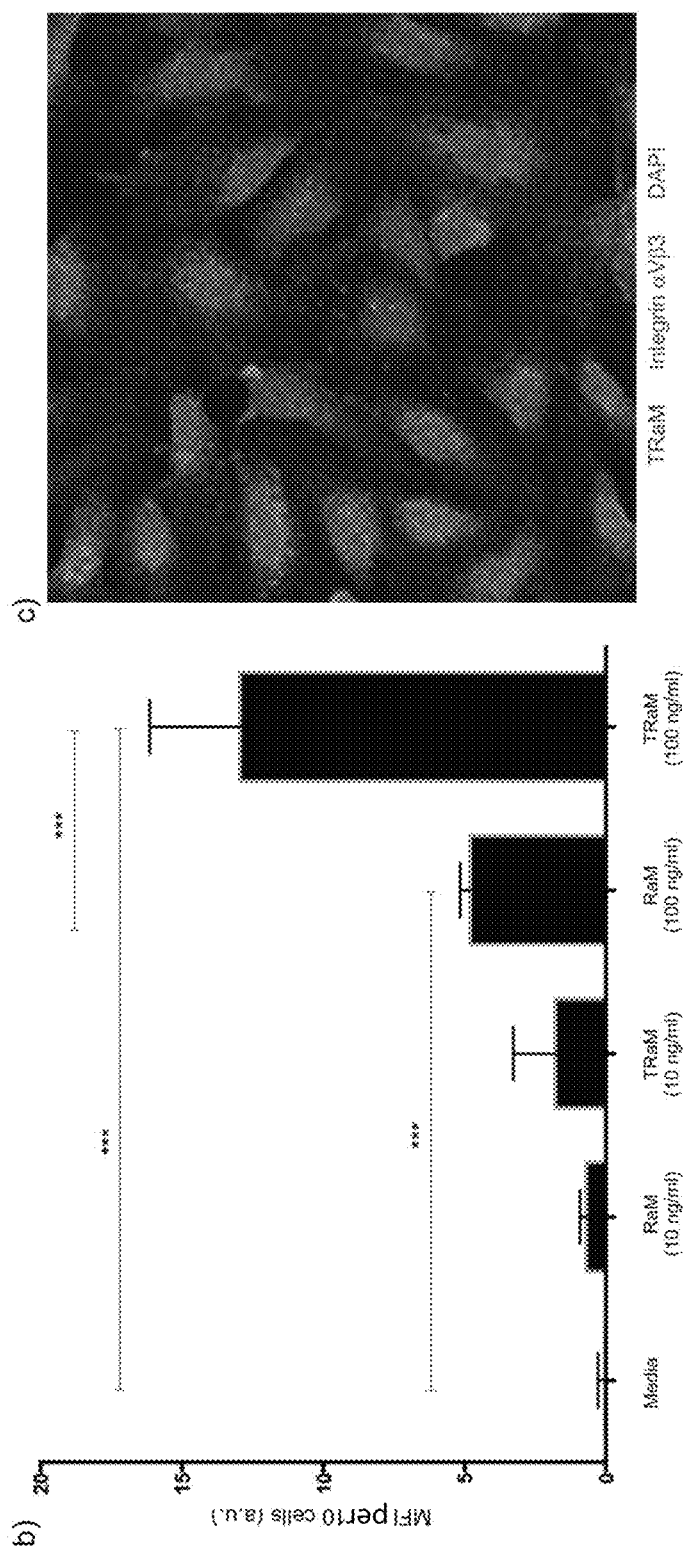
Figure 4:
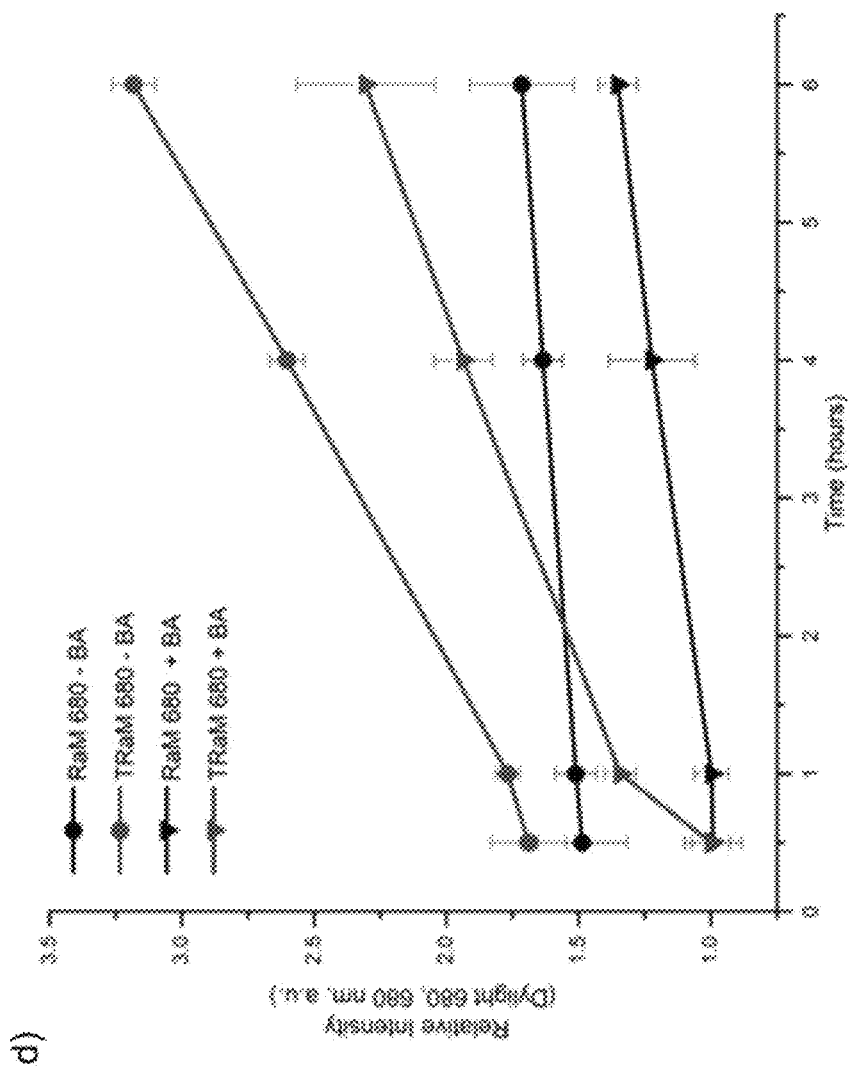

Human umbilical vein Ecs (HUVECs) and mouse cardiac endothelial cells (MCECs) were pre-treated for 6 hours with escalating doses of TraM, RaM, empty micelles or free rapamycin to assess cellular toxicity (FIG. 3). M-Per lysis of Ecs was used as an assay control. After 6 hours of pre-treatment, a four hours MTS assay was performed as a colorimetric method for determining the number of viable, metabolically active cells. Nanoparticles with and without a therapeutic payload, along with free rapamycin showed no significant toxic effects on either EC lines (FIG. 3a, b). Additionally, at escalating doses, TraM nanoparticle therapy exhibited no significant toxic effects on either MCECs (FIG. 3c) or HUVECs (not shown). This lack of toxicity is not significantly different from that seen in free drug treated mouse and endothelial cells. Treatment with 3000 ng $ml^{-1}$ did induce toxicity; however, this was seen in both free drug and TraM treated groups, for both cell lines.

Example 3

Intracellular Uptake

Micelles were functionalized with a cRGD peptide to target the αVβ3 integrin on EC surfaces to facilitate targeting and cellular uptake (FIG. 4a). To examine the intracellular uptake of RaM and TraM, human EC were incubated with these constructs for 6 and 24 hours periods and subsequently examined for micelle accumulation by visualization of the Dylight 680 fluorophore (red) on the micelles surface by confocal microscopy. Internalization was observed as early as 6 hours after incubation and internalization was concentration dependent (FIG. 4b). Targeting with cRGD significantly improved the micelle internalization by more than 50% as compared to untargeted RaM. αVβ3 integrin is well-characterized for its function related to angiogenesis as well as its expression on human EC. Additionally, cRGD has also been established as a prime candidate for targeting cells expressing αVβ3 integrin. (See A. Adulnirath, S. W. Chung, J. Park, S. R. Hwang, J. Y. Kim, V. C. Yang, S. Y. Kim, H. T. Moon and Y. Byun, *Journal of controlled release: official journal of the Controlled Release Society*, 2012, 164, 8-16). It was confirmed the expression of αVβ3 integrin on the HUVEC cells used within these experiments and show in FIG. 4c the presence of TraM within these αVβ3 integrin-expressing HUVECs.

To demonstrate that uptake of TraM were predominantly due to endocytosis associated with the cRGD peptide and not diffusion of the micelles, HUVEC were treated with brefeldin A (BA), a fungal metabolite that reversibly interferes with intracellular transport and receptor cycling and examined for uptake (FIG. 4d). BA acts by inducing major structural changes in the morphology of endosomes, the trans-Golgi network, and lysosomes by causing the formation of an extensive tubular network and preventing new endosome formation. (See W. Hunziker, J. A. Whitney and I. Mellman, *Cell*, 1991, 67, 617-627). As seen previously, significant fluorescence was observed when HUVEC were incubated with TraM (−BA, 88% increase) over a 6 hours period. Fluorescence intensity increased by only 36% when HUVEC were treated with RaM (−BA). Pre-incubation with BA (+BA) decreased the relative fluorescence intensity of TraM incubated cells by ~38% over time. RaM uptake was inhibited to a lesser extent with BA.

In further detail, HUVEC cells were plated on 25×25 mm coverslips at a density of 30,000 cells per coverslip and maintained overnight in media at 37° C. in an incubator supplied with 5% $CO_2$. Twenty four hours after plating, one set of cells were treated with 250 μl of brefeldin A (BA) solution (10 μg ml$^{-1}$ in media) and were incubated for 1 hour (+BA). Another set of coverslips was left with 250 μl of media as −BA controls. For the +BA set of cells, the BA solution in media was replaced with 250 μl of 500 nM RaM 680 or TraM 680 solutions. The −BA cells were treated with 250 μl of 500 nM RaM 680 or TraM 680 solutions. Both set of cells were incubated with the NPs for 0.5, 1, 4 and 6 hours respectively. After treatment, the cells were washed with media and then fixed with 4% paraformaldehyde for 10 minutes followed by three washes with PBS buffer. For staining of nuclei, cells were incubated with DAPI. Uptake and co-localization of NPs were visualized by fluorescence microscope using a Leica DM 4000B microscope (Leica Microsystems, IL). The images were analyzed using ImageJ (NIH, MA) software for relative normalized intensities for comparison analysis.

Example 4

Biological Efficacy

Figure 5:
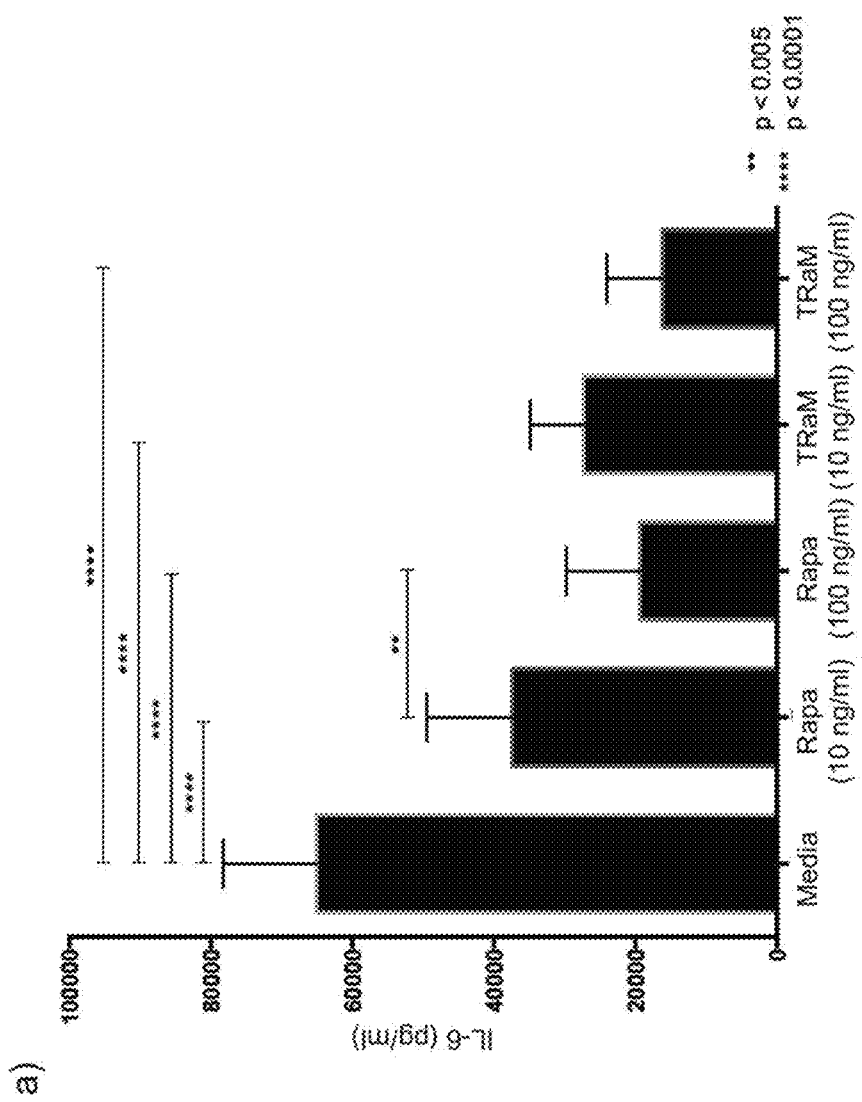
FIG. 5 shows the suppression of EC inflammation by TRaM internalization and release. ELISA were performed to assess the ability of TRaM to suppress biomarkers of EC inflammation. IL-6 (a) and IL-8 (b) were analyzed as markers of EC activation. HUVEC were subjected to oxidative stress with $H_2O_2$ and treated with either free rapamycin or TRaM (10 or 100 ng ml$^{-1}$). IL-6 and IL-8 were significantly suppressed by TRaM nanotherapy when compared to media alone, showing biological efficacy of targeted immunosuppressant nanotherapy in vitro, and had a similar effect as free rapamycin (IL-6: **P<0.0001; p<0.005; IL-8: *p<0.05; p<0.005), c) C57BL/6 mice were inoculated with MCEC from allogeneic FVB mice. T lymphocytes were then isolated from splenocytes 14 days later. Sensitized T cells were co-cultured with MCEC, which were either left untreated or pre-treated for 6 hours in a hypoxic chamber at 4° C. with free rapamycin or TRaM to mimic cold storage ischemia, d) Production of mouse IL-8 (KC) by stimulated MCEC was significantly dampened by rapamycin and TRaM therapy (p≤0.01; **p≤0.001), e) T cell production of IFN-γ was also significantly reduced in co-cultures when treated with free drug and TRaM therapy (**p≤0.001).
Figure 5:
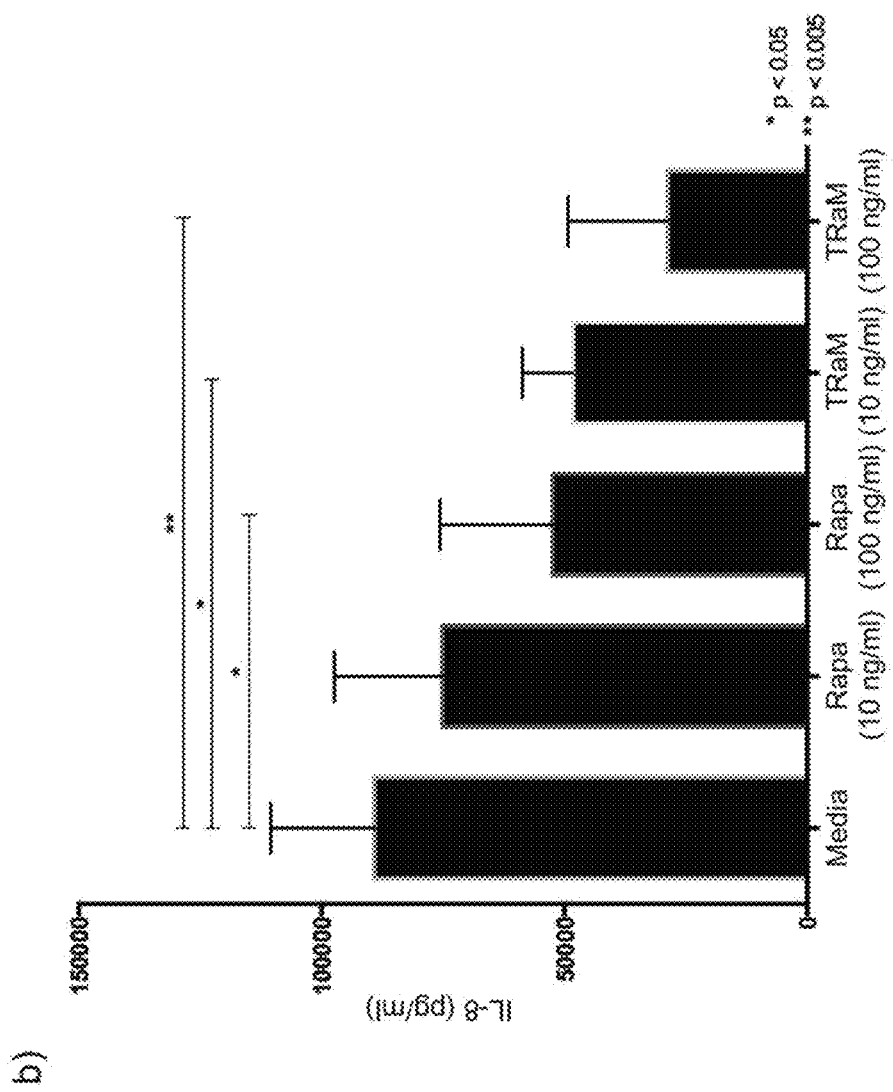
Figure 5:
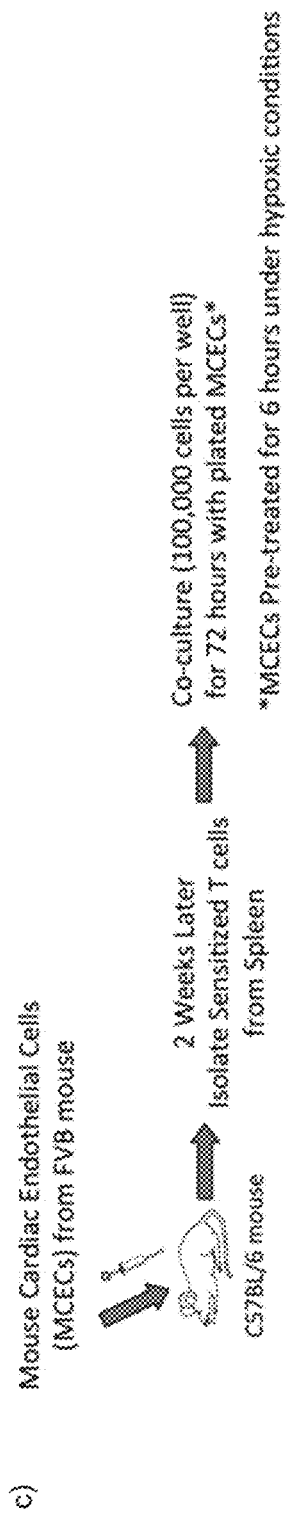
Figure 5:
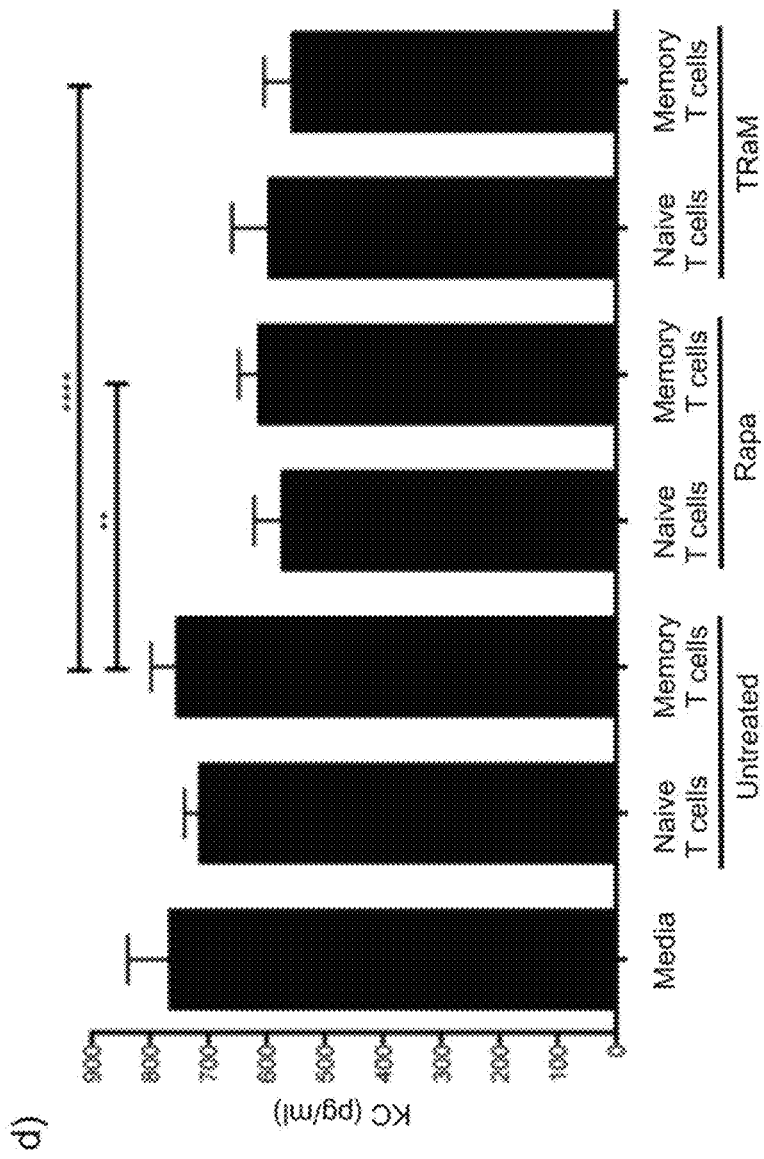
Figure 5:
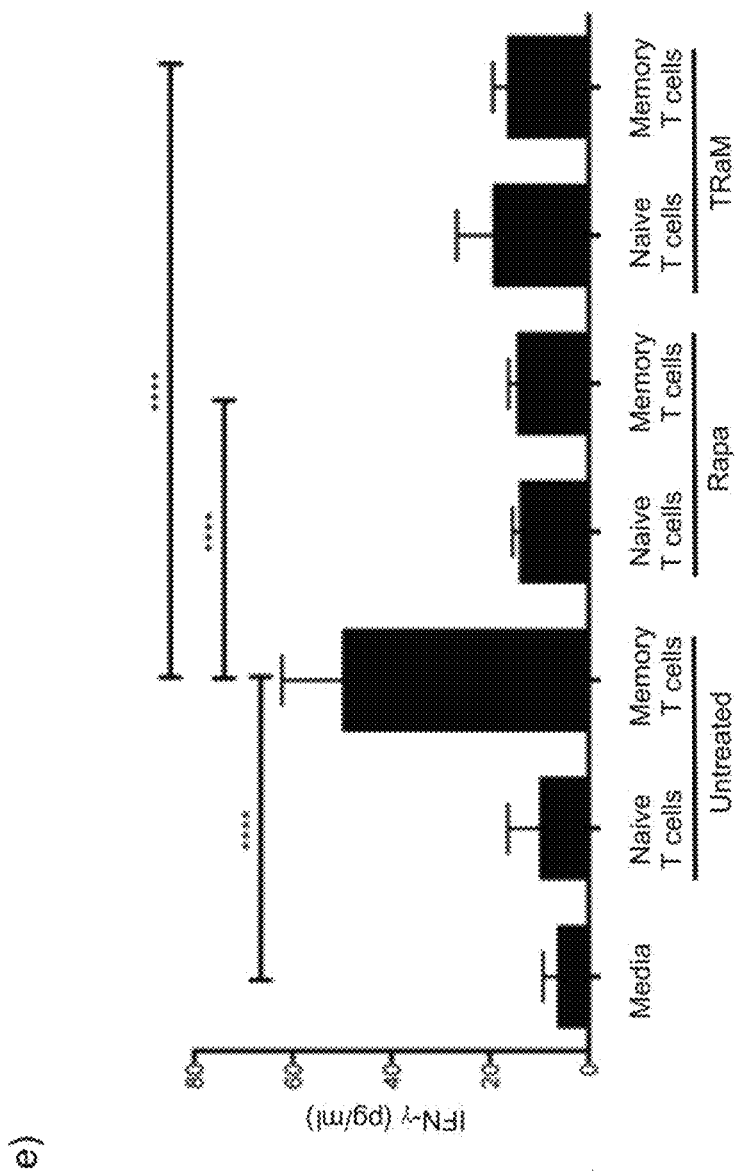

Biologic efficacy of these novel targeted micelles was assessed. To determine the potential impact of local targeted delivery of rapamycin for later translation to organ transplantation, in vitro culture experiments were performed using a cell system to model the impact of reperfusion injury on EC activation and antigen presentation capacity (FIG. 5). The endothelium is the first site of donor organ interface with the recipient and is particularly susceptible to ischemia reperfusion injury. Further, the endothelium plays an important role in priming of the adaptive immune system, which contributes to the tempo and severity of the recipient rejection response. Human primary HUVEC that mimic the in vivo vascular target was treated with $H_2O_2$, in order to mimic the oxidative stress that occurs during the ischemia/reperfusion phase of solid organ transplantation (FIG. 5a, b). Cells were treated with 10 ng ml$^{-1}$ or 100 ng ml$^{-1}$ of free rapamycin or the TraM constructs. (See Y. S. Kwon, H. S. Hong, J. C. Kim, J. S. Shin and Y. Son, *Investigative ophthalmology & visual science,* 2005, 46, 454-460). Oxidative injury to endothelial cells induces endothelial activation, which results in a pro-inflammatory phenotype that is characterized by the production and release of the pro-inflammatory cytokines, IL-6 (FIG. 5a) and IL-8 (FIG. 5b). H202 exposure significantly increased EC production of IL-6 and IL-8 and TraM therapy significantly blunted this response.

Along with IM, memory T cell responses remain a barrier to achieving tolerance in organ transplantation. To test the ability of TraM to reduce cold storage, IR-induced endothelial activation, and memory T lymphocyte-induced injury, MCECs from FVB mice were used to inoculate allogeneic C57BL/6 mice. Sensitized T cells from the spleens of these mice were isolated using magnetic cell sorting 14 days later and co-cultured with MCEC in UW solution at 4° C. in a hypoxic chamber with or without TraM therapy (100 ng ml$^{-1}$). Efficacy of TraM therapy was assessed by measuring mouse IL-8 (KC), a marker of EC activation, from MCEC and IFN-γ, a T cell cytokine, by T cells. As shown in FIG. 5, biomarkers of inflammation in a clinically relevant model of cold ischemia are significantly reduced by both EC and T cells when treated with TraM therapy on par with the standard of care (FIG. 5c-e). These data suggest that targeted drug delivery demonstrates equivalent efficacy to standard therapy in the face of oxidative stress induced injury and can uniquely down regulate memory T cell responses in a novel, model of cold-storage hypoxia.

Figure 6:
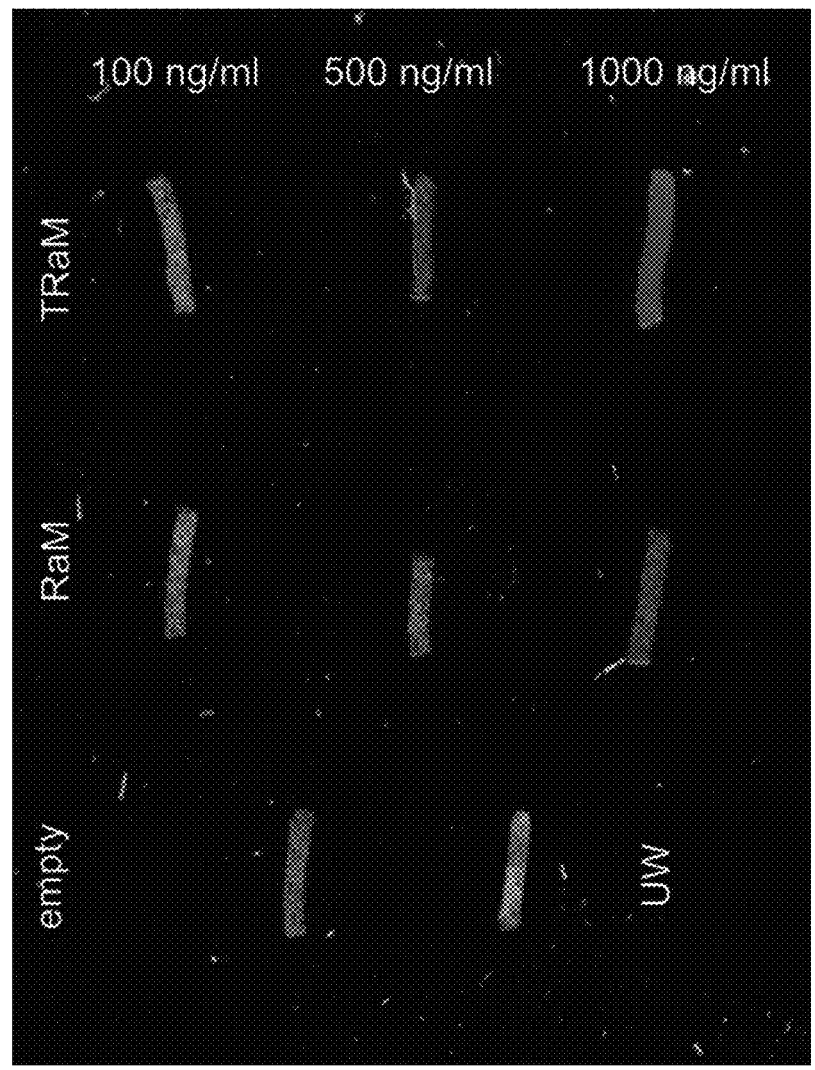
FIG. 6 shows the delivery of TRaM to aortic grafts with dose-dependent uptake. Aortas surgically removed from mice were incubated over 6 hours with TRaM (top), RaM (middle), empty micelles (bottom left), or cold UW solution (bottom right). The organs were imaged using ex vivo fluorescence imaging. Multispectral analysis was conducted to reveal fluorescence (680 nm) due only to intact micelles (red).

Further, it was determined whether encapsulated rapamycin would accumulate in aortic grafts soaked for 6 hours in cold UW solution containing increasing concentrations of TraM (FIG. 6). Spectral analysis revealed uptake of TraM and RaM in a dose-dependent fashion, beginning with as little as 500 ng ml$^{-1}$ in ex vivo aortas. Little micelle uptake was observed in aorta grafts incubated with RaM or empty micelles. The micelles remained intact over the 6 hours period as observed by fluorescence.

Figure 7:
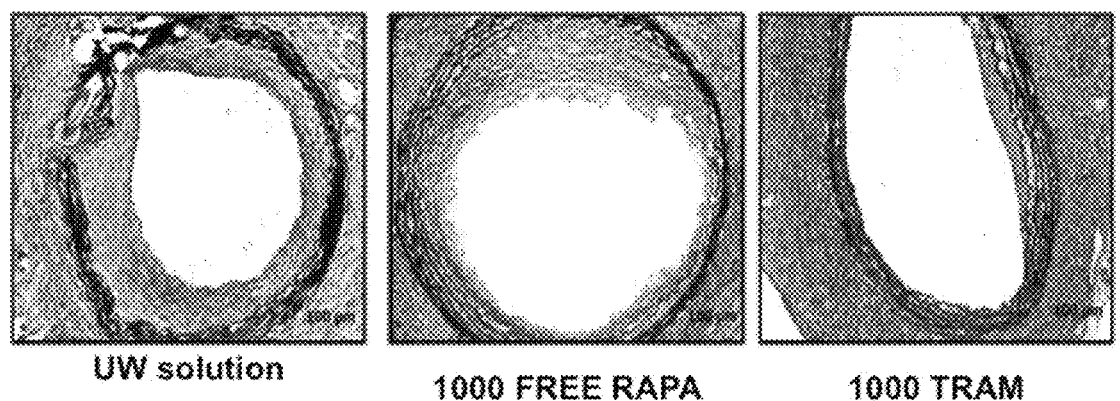
FIG. 7 Shows that delivery of TRaM or Free Rapamycin contained within Belzer UW solution to aortic allografts prior to transplantation reduces the characteristic intimal thickening associated with chronic allograft rejection (A). Further, that quantification of chronic rejection in pre-treated allografts shows that TRaM significantly reduce intimal thickening when compared to UW alone, or UW supplemented with 1000 ng/ml of Free Rapamycin (*p<0.01).
Figure 7:
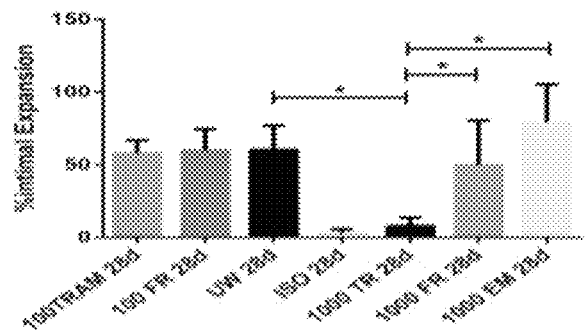

To test the in-vivo functionality of rapamycin augmentation of Belzer UW solution, the aortic allograft model was utilized. The aortic allograft is a well-accepted model of chronic allograft rejection. Aortic allografts were harvested from Balb/c donors and placed in Belzer UW solution containing either Free rapamycin or TRaM at concentrations of either 100 or 1000 ng/ml for a period of 6 hrs and stored at 4° C. Following cold storage grafts were implanted into the abdominal descending aorta of C57Bl/$_6$ recipient mice and allografts harvested at 28 days post transplant. Grafts were histologically processed, sectioned and stained with Elastic Van Gieson stains to assess the degree of allograft rejection. FIG. 7A shows representative images from transplanted grafts, which clearly demonstrates that TRaM and Free Rapamycin pre-treatment during allograft storage significantly reduces intimal thickening (blocking of the vessel lumen), a key feature of allograft rejection. Further, note that TRaM provides significantly more protection from intimal thickening than Free Rapamycin. The intimal thickening was quantified, FIG. 7B, note that only a dose of 1000 ng/ml provided protection and that TRaM provided the most significant reduction in allograft rejection as marked by intimal thickening.

Example 5

Pre-Treatment Formulation

TraM was added/dissolved to/in Belzer UW cold storage solution at a concentrations of 100 ng/ml and stored at 4° C. until use. In another embodiment, TraM was added/dissolved to/in Belzer WV cold storage solution at a concentration of 1000 ng/ml and stored at 4° C. until use.

It is to be understood that the invention is not limited to the particular embodiments of the invention described above, as variations of the particular embodiments may be made and still fall within the scope of the appended claims.

What is claimed is:

1. A formulation to pre-treat an organ prior to transplantation, comprising:
   a) a first composition comprising a therapeutically effective amount of an immunosuppressive agent encapsulated in a nanocarrier that comprises on its surface a targeting moiety; and
   b) a second composition comprising a preservation solution, wherein said targeting moiety is a peptide or peptidomimetic that binds Complement component 3 (C3) breakdown products and reperfusion epitopes, wherein the peptide or peptidomimetic comprises a Complement Receptor type 2 (Cr2) peptide or peptideomimetic;
   wherein the nanocarrier is a polymeric nanoparticle, micelle, or liposome.

2. The formulation according to claim 1, wherein said immunosuppressive agent comprises a mammalian target of rapamycin inhibitor, a calcineurin inhibitor or a combination thereof.

3. The formulation according to claim 1, wherein said immunosuppressive agent is rapamycin or a derivative thereof or combinations thereof.

4. The formulation according to claim 1, wherein the immunosuppressive agent comprises tacrolimus or a derivative thereof or combinations thereof.

5. The formulation according to claim 1, wherein the immunosuppressive agent comprises cyclosporin A or a derivative thereof or combinations thereof.

6. The formulation according to claim 1, wherein the immunosuppressive agent comprises a nuclear factor kappa-light-chain-enhancer of activated B cells (NFkB) inhibitor.

7. The formulation according to claim 1, wherein the immunosuppressive agent comprises a Janus kinase 3 (JAK3) inhibitor.

8. The formulation according to claim 1, wherein the immunosuppressive agent comprises Interleukin 2 (IL-2) R alpha or a derivative thereof or a combination thereof.

9. The formulation according to claim 1, wherein the immunosuppressive agent comprises Complement C siRNA.

10. The formulation according to claim 1, wherein said immunosuppressive agent is encapsulated in a micelle.

11. The formulation according to claim 1, wherein the immunosuppressive agent comprises mycophenolate or a derivative thereof or a combination thereof.

12. The formulation according to claim 1, wherein said nanocarrier encapsulating said immunosuppressive agent has a mean diameter of 5 nm to 100 nm.

13. The formulation according to claim 1, wherein said nanocarrier encapsulating said immunosuppressive agent has a mean diameter of 10 nm to 15 nm.

14. The formulation according to claim 1, wherein said nanocarrier is pH sensitive, temperature sensitive or combinations thereof.

15. The formulation according to claim 10, wherein the micelle comprises N-palmitoyl homocysteine.

16. The formulation according to claim 10, wherein the micelle comprises amino-polyethylene glycol-phosphatidylethanolamine.

17. The formulation according to claim 1, wherein said targeting moiety comprises the amino acid sequence Arg-Gly-Asp.

18. The formulation according to claim 1, wherein said targeting moiety comprises a cyclized Arg-Gly-Asp peptide or peptidomimetic.

19. The formulation according to claim 1, wherein said preservation solution is selected from the group consisting of a sterile non-pyrogenic solution, University of Wisconsin cold storage solution, Kyoto ET Solution, Phosphate Buffered Sucrose Solution, Bretschneider Histidine Tryptophan Ketoglutarate (HTK) Solution, Ross-Marshall Citrate Solution, and Euro-Collins Solution.

20. The formulation according to claim 1, wherein first composition is at a concentration of from 100-2000 ng/ml.

21. A method for pre-treating an organ prior to transplantation, comprising the step of administering to said organ in need thereof a therapeutically effective amount of the formulation of claim 1.

22. The method according to claim 21, wherein said composition suppresses an allo-immune response in said organ.

23. The method according to claim 21, wherein said immunosuppressive agent comprises a mammalian target of rapamycin inhibitor, a calcineurin inhibitor or a combination thereof.

24. The method according to claim 21, wherein said immunosuppressive agent (a) is rapamycin or a derivative thereof or combinations thereof, (b) comprises tacrolimus or a derivative thereof or combinations thereof or (c) comprises cyclosporin A or a derivative thereof or combinations thereof.

25. The method according to claim 21, wherein the immunosuppressive agent comprises a nuclear factor kappa-light-chain-enhancer of activated B cells (NFkB) inhibitor.

26. The method according to claim 21, wherein the immunosuppressive agent comprises a Janus kinase 3 (JAK3) inhibitor or Complement C siRNA.

27. The method according to claim 21, wherein the immunosuppressive agent comprises Interleukin 2 (IL-2) R alpha or a derivative thereof or a combination thereof.

28. The method according to claim 21, wherein said immunosuppressive agent is encapsulated in a micelle.

29. The method according to claim 21, wherein the immunosuppressive agent comprises mycophenolate or a derivative thereof or a combination thereof.

30. The method according to claim 21, wherein said nanocarrier encapsulating said immunosuppressive agent has a mean diameter of 5 nm to 100 nm.

31. The method according to claim 21, wherein said nanocarrier encapsulating said immunosuppressive agent has a mean diameter of 10 nm to 15 nm.

32. The method according to claim 21, wherein said nanocarrier is pH sensitive, temperature sensitive or combinations thereof.

33. The method according to claim 21, wherein the micelle comprises N-palmitoyl homocysteine or amino-polyethylene glycol-phosphatidylethanolamine.

34. The method according to claim 21, wherein said targeting moiety comprises the amino acid sequence Arg-Gly-Asp.

35. The method according to claim 21, wherein said targeting moiety comprises a cyclized Arg-Gly-Asp peptide or peptidomimetic.

36. The method according to claim 21, wherein said preservation solution is selected from the group consisting of a sterile non-pyrogenic solution, University of Wisconsin cold storage solution, Kyoto ET Solution, Phosphate Buffered Sucrose Solution, Bretschneider Histidine Tryptophan Ketoglutarate (HTK) Solution, Ross-Marshall Citrate Solution, and Euro-Collins Solution .

37. A method for suppressing an immune response or organ transplant rejection in a transplant recipient in need thereof, comprising the step of pre-treating an organ prior to transplantation comprising the step of administering to said organ a therapeutically effective amount of the formulation of claim 1.

38. The formulation according to claim 1, wherein said targeting moiety is a combination of the peptide or peptidomimetic that binds Complement component 3 (C3) breakdown products and reperfusion epitopes, and a peptide or peptidomimetic that binds an integrin, wherein the peptide or peptidomimetic comprises the amino acid sequence Arg-Gly-Asp (RGD).

39. The formulation according to claim 3, wherein said immunosuppressive agent is encapsulated in a micelle.

* * * * *